United States Patent [19]
Heck et al.

[11] Patent Number: 5,845,002
[45] Date of Patent: Dec. 1, 1998

[54] METHOD AND APPARATUS FOR DETECTING SURFACE FEATURES OF TRANSLUCENT OBJECTS

[75] Inventors: Richard D. Heck, Riverside; Henry A. Affeldt, Victorville, both of Calif.

[73] Assignee: Sunkist Growers, Inc., Ontario, Calif.

[21] Appl. No.: 334,165

[22] Filed: Nov. 3, 1994

[51] Int. Cl.[6] ........................................................... G06K 9/00
[52] U.S. Cl. .................... 382/110; 382/142; 209/588; 348/127; 348/128; 348/131; 348/164
[58] Field of Search .................... 382/110, 141, 382/142; 209/588, 511; 348/127, 128, 131, 164, 89, 91; 356/239, 240, 237, 52, 337, 338

[56] References Cited

U.S. PATENT DOCUMENTS

| | | | |
|---|---|---|---|
| 1,943,278 | 1/1934 | Thompson et al. | 209/588 |
| 3,549,890 | 12/1970 | Keller | 382/142 |
| 3,768,645 | 10/1973 | Conway et al. | 209/111.5 |
| 3,930,994 | 1/1976 | Conway et al. | 209/74 M |
| 3,932,042 | 1/1976 | Faani et al. | 356/240 |
| 4,055,834 | 10/1977 | Planke | 382/142 |
| 4,376,951 | 3/1983 | Miyazawa | 356/240 |
| 4,608,709 | 8/1986 | Hedler et al. | 382/142 |
| 4,741,042 | 4/1988 | Throop et al. | 382/110 |
| 4,760,270 | 7/1988 | Miller | 250/563 |
| 5,007,096 | 4/1991 | Yoshida | 382/142 |
| 5,026,982 | 6/1991 | Stroman | 250/223 |
| 5,164,795 | 11/1992 | Conway | 348/89 |
| 5,174,429 | 12/1992 | LaVars et al. | 198/372 |
| 5,321,491 | 6/1994 | Summers et al. | 382/110 |

FOREIGN PATENT DOCUMENTS

| | | |
|---|---|---|
| 0058028 | 8/1982 | European Pat. Off. . |
| 0566397 | 10/1993 | European Pat. Off. . |

*Primary Examiner*—Christopher S Kelley
*Attorney, Agent, or Firm*—Linda M. Robb; Daniel L. Dawes

[57] ABSTRACT

The topographic surface features of a translucent object, such as a citrus fruit with a peel, are scanned and evaluated to permit the classification thereof according to its surface features. In the case of citrus fruit, the coarseness or pebbliness, puff and crease, ridge and valley, cuts, punctures, scrapes and splits, clear rot or sour rot of the peel is optically identified through digital analysis of the pixel scans and sorted based upon the peel surface quality. The object is classified by separating the scanned image of the fruit from the background image and removing the background image. A statistical evaluation of the image of the object as a whole, including both hemispheres of the object, is made to determine if there is any surface feature variation which might qualify as a defect or be a suitable basis upon which a classification judgment can be made. If there is, the object image is subject to high frequency or low pass filtering and thresholding of the pixel intensities to derive a refined image. The refined image is then tabulated or organized into neighborhoods contiguous to sharp transitions or gradual transitions to identify specific areas defined as blobs which, when compared against a given minimum area, shape requirement and/or width can be identified as one of the surface imperfections sought.

19 Claims, 20 Drawing Sheets

METHOD AND APPARATUS FOR DETECTING SURFACE FEATURES OF TRANSLUCENT OBJECTS

BACKGROUND OF THE INVENTION

1. Field of the Invention

The invention relates to the field of methods and apparatus for topographic analysis of the surface texture and integrity of objects and sorting those objects based upon such surface analysis, and in particular relates to a method and apparatus for optically analyzing the surface region of fruit, and in particular citrus fruit, so that the fruit can be sorted according to selected surface characteristic criteria.

b 2. Description of the Prior Art

Apparatus and methods for automatically evaluating citrus fruit on the basis of presumed transparency to light rays and then selectively separating them according to such evaluation in a conveyor system have been described by Conway, "Method and Means for Internal Inspection Sorting of Produce," U.S. Pat. No. 3,930,994 (1976), assigned to the same assignee as the present invention.

Conway's goal is to determine the extent of frost damage to the meat of the fruit. To do so, he orients the fruit on a conveyor between a pair of high intensity light sources—such as quartz iodine tungsten filament lamps, X-ray beam generators or lasers—and a pair of detectors positioned to straddle the fruit core. The detectors are photomultiplier tubes whose collimating openings receive light transmitted through—i.e., not absorbed or scattered within—the fruit. The signals from the detectors are coupled to an internal analysis computer controlled by timing sensors to compare the instantaneous outputs from the two detectors and thus measure the extent of internal damage in the fruit (presumed from preselected differences in the two readings), after which the fruit is separated according to the extent of damage thus noted.

Recognizing that the skin portion of the fruit has different optical absorption and scattering characteristics than the meat portion, Conway regards as error signals, which require elimination, the signals obtained by the detectors when their readings correspond to light detected from the peel portion of the fruit. See column 6, lines 32–43. To avoid obtaining any readings from the skin of the citrus fruit, Conway uses two timing sensors to begin damage evaluation of the meat portion only after a detector has ceased to receive light scattered within and projected from the peel portion and begun to receive light transmitted through the meat portion of the fruit, and to end evaluation before the detector again receives light scattered within the peel portion as the fruit progresses down the conveyor between the incident light beam and the light transmission detector.

However, even reliably detecting the optical characteristics of the meat portion of citrus fruit has proved to be an extremely difficult task through such optical means. Light in most frequencies does not simply transmit through a fruit, as if the fruit were a transparent object, such as a crystal ball. Rather, it is absorbed by, and scatters within the fruit. Thus, small structures can not be reliably identified, and only massive frost damage can be reliably detected even by detection of the fruit interior using an X-ray beam, to which fruit is more transparent, as described generally in U.S. Pat. No. 3,768,645.

Also, while detecting and eliminating fruit which has damaged meat portions has substantial value, a sorting function of even greater value is the ability to separate fruit into categories based upon the nature of its surface texture or the integrity of its skin or peel. For example, a carton of unblemished oranges with sound peels will generally fetch a higher price in the market than a carton of oranges that exhibit a variety of skin blemishes and textures, and/or defects, even though the meat portion of both is acceptable, and even if the interior of some fruit may be slightly damaged.

An analogy may be made to eggs. By this analogy, the prior art, as exemplified by the foregoing Conway reference, is similar to the process of candling eggs—i.e., viewing them from the opposite side of a high-intensity incident light beam to detect blood spots or other imperfections within. The interior portion of an egg—the yolk and white—and not the shell is of dominating importance. By analogy, Conway seeks to examine the interior portion of the fruit, and not the peel or outer surface. By contrast, the present invention is concerned not with the internal contents of the object to be classified and sorted, but rather with topographic appearance and integrity of the outer "covering" of the object.

While the external surface textures of citrus fruit or any other objects can be visually determined and manually assessed by human quality control operators, the cost and reliability factors of such human sorting can in many cases become unacceptable. Furthermore, human operators cannot see into the layers of the fruit beneath the outer surface because of the health risk inherent in extended eye exposure to the high light intensities required to generate enough scattered light to make the peel glow sufficiently to make the underlying peel depth visible. And humans cannot see near infrared light, which has superior depth penetration through the fruit and into the fruit peel, as compared with visible light.

Therefore, what is needed is an intelligent, automatic means for optically examining the outer surface and surface region of an essentially translucent or transparent object, determining the nature of the surface texture and outer region integrity, and then making a selection decision based on such determination.

BRIEF SUMMARY OF THE INVENTION

The present invention is a method and apparatus for sorting objects which are essentially translucent. Fruit, particularly citrus fruit, can be sorted in accordance with the invention. As further discussed hereinbelow, many other types of objects can thus be sorted, if such objects are essentially translucent or transparent to the particular light frequency selected. For the sake of convenience, specific reference herein will often be made to fruit (referring particularly to citrus fruit), although it is to be understood that all such objects are included.

The fruit is sorted according to the surface region features thereof, and the method comprises illuminating each of them to scatter light within them and through their surface region. In the case of fruit, with which the preferred embodiment of this invention is primarily concerned, each is illuminated such that light scattered within the fruit causes the fruit to glow. This glow, which is transmitted out through the surface region, is detected, and images of the entire glow pattern are thus obtained.

It has been found, in the course of reducing this invention to practice, that defects on or near the outer surface appear considerably more clearly than internal defects, as previously sought by Conway, who ignored surface blemishes. Therefore, each such instantaneous image constitutes a matrix of data corresponding to the surface and near-surface features of the fruit. Each detected image is converted to data for analysis to determine if the surface feature(s) sought is/are present. This may be accomplished by comparing the data with selected criteria, and the fruit may thus be classified according to the analyzed data to identify those falling within selected categories, based on the observed surface feature data. The classified fruit may then be sorted in accordance with the selected definitions of such categories. This permits automatic classification and sorting of the fruit according to its surface region features.

The data in the images must be processed to enable pattern recognition of the surface features of the fruit. Prior to such processing of the data, scanned data not originating from light scattered through the surface features of the object is removed. A statistical measure of the surface features is derived to determine if a sufficient variation of the surface features over substantially all of the surface of each the fruit is great enough to indicate a surface defect.

Processing the data normally further comprises selecting the data scanned from the surface features by filtering the data by frequency, relative to a predetermined frequency cutoff. In some such situations data filtering comprises passing only high frequency data components. In other such situations data filtering comprises passing only low frequency components of the data.

The fruit glow image is typically scanned to collect the necessary data, and if so, that step normally comprises scanning the fruit along a predetermined line traversing the object. It is also contemplated that the fruit can be scanned along a plurality of lines. Each scan may be oriented at the same or another angle traversing the object.

The method may further comprise optically forming an image of the fruit that simultaneously includes all or a substantial portion of its surface features. Where the fruit is generally spherical, as in the case of many varieties of citrus fruit, forming the image comprises forming a separate image of substantially each hemisphere.

In the illustrated embodiment, scanning the fruit is optically performed by reflecting an image of the illuminated fruit (i.e., the glow emanating therefrom) into a scanning camera pointed away from the illuminated fruit, so that direct transmission of light into the camera is avoided. This can also be done merely by pointing the camera at an angle relative to the direction of the incident fruit illumination beam. It should be noted, however, that the method of this invention can be used even if the camera points directly toward the incident beam, since most of the light detected by the camera will have been scattered within the fruit, to produce a resultant glow projected through its surface region. And in that case, particularly if the beam consists of an LED (light emitting diode) or laser source, fruit sensing and timing means coupled therewith can be used to prevent damage to the camera which might be caused by light directly detected, i.e., without an intervening fruit.

In general the method classifies the fruit according to their topographic surface features. With citrus fruit (having relatively thick peels), such categorizing may comprise classifying their peels according to porosity, puff and crease, ridges and valleys, fractures, decomposition and other selected factors.

Scanning comprises scanning a two dimensional array to provide a two dimensional graphic image of the topographic surface features of the fruit. Illuminating the fruit comprises illuminating it by means of a selected light generating means which projects light of a selected frequency or combination of frequencies.

Processing of the data also comprises segmenting the scanned image into a background and object, and removing the background from the scanned image, leaving primarily the object.

Classifying the citrus fruit according to porosity of the peel comprises filtering the scanned image for high frequency data using a high pass data filter. A threshold of pixel intensity of the filtered image is established. The number of pixels having an intensity above the established threshold is tabulated to identify porosity of the peel.

Classifying the citrus fruit by puff and crease on the outer surface of the peel comprises filtering the image for low frequency data using a low pass/smoothing data filter. A pixel intensity threshold for the filtered image is established. The number and distribution of the pixels having an intensity above the threshold is tabulated to identify puff and crease on the outer surface of the peel.

Classifying according to raised and recessed wedges, or fractures, in the peel comprises selectively scanning the image for transitions in pixel intensity. A threshold of pixel intensity and transition rate is established. The number of pixels having an intensity above the established threshold in neighborhoods contiguous to pixel boundaries corresponding to intensity transitions is tabulated. The neighborhoods are defined as blobs. The number of blobs which exceed a predetermined characteristic parameter is tabulated to identify raised and recessed wedges in the peel. The characteristic parameter is a predetermined minimum area of the blob, and tabulating the number of blobs to identify raised and recessed wedges in the peel comprises tabulating the number of blobs which exceeds the predetermined minimum area. Or the characteristic parameter may be shape, and tabulating the number of blobs to identify the raised and recessed wedges then comprises tabulating the number of the blobs having a shape complying with the predetermined shape definition. Similarly, identification of a fracture is based on a narrow, sharp discontinuity in intensity.

Classifying by surface decomposition comprises scanning the image of the citrus fruit for more gradual transitions in pixel intensity. A predetermined threshold is established. The number of pixels having an intensity above the predetermined threshold in neighborhoods contiguous to pixel boundaries with gradual transitions is tabulated. The neighborhoods are defined as blobs. The number of the blobs which exceed a given characteristic parameter is tabulated to identify the surface decomposition.

The predetermined threshold(s), shape, area, width and characteristic parameter(s), as appropriate in any of the foregoing grading methods, can be selectively established as a function of the size of the citrus fruit, which can be detected and automatically input according to well known methods.

The invention may also be characterized as an apparatus for sorting objects which are essentially translucent, such as citrus fruit, or essentially transparent—to the light frequency or frequencies selected—according to surface region features of the objects. Such apparatus includes an inspection station and at least one sorting station. A conveyor moves the objects through the inspection station and to the sorting station. A sorter at the sorting station sorts the objects according to classification of the surface features of the objects by selective diversion of objects from the conveyor. A computerized optical scanner generates a graphic image of the object at the inspection station and evaluates the surface features of the object according to at least one topographic characteristic of the surface feature. The objects are thus categorized and sorted according to the surface features.

In one embodiment by which citrus fruit is sorted, the computerized optical scanner comprises two independent illuminating/scanning light and camera assemblies at the inspection station. In that embodiment, the computerized optical scanner may comprise two lens-focused tungsten Halogen light sources disposed at approximately 120 degrees from a vertical plane through the inspection station for illuminating the fruit, and a scanning camera, corresponding to each light source, for scanning the fruit, which camera is not aligned with either of the light sources. In this embodiment, the camera is turned away from the fruit, and the computerized optical scanner further comprises a plurality of mirrors for reflecting, into that camera, an image of the glow generated within the fruit and transmitted through the peel.

More generally, the invention comprises an apparatus for classifying objects based on a scattered light intensity pattern comprising at least one source of light directed onto the object. A sensing element converts the light scattered within the object and transmitted out through the surface thereof into digital data. An evaluation computer classifies the object according to topographic surface features of the object derived from analysis of the digital data. As a result, the objects are optically classified in preparation for sorting them.

The invention may now be better visualized by turning to the following drawings wherein like elements are referenced by like numerals.

BRIEF DESCRIPTION OF THE DRAWINGS

FIG. 3a is a computer image of a smooth fruit peel as generated by the invention, while

FIG. 4a is a computer image of a fruit having sour rot as generated by the invention, while FIG. 4b is a histogram again taken through a selected scan line of the fruit of FIG. 4a.

FIG. 5a is a computer image of fruit as generated by the invention showing clear rot, while FIG. 5b is a histogram taken through a selected scan line of the fruit of FIG. 5a.

FIG. 6a is a computer image of fruit having a pebbled peel as determined by the invention, while

FIG. 7a is a computer image of fruit showing soft puff and crease as detected by the invention, while

FIG. 8a is a computer image of fruit with ridge and valley defects as determined by the invention, while FIG. 8b is a histogram taken along a selected scan line of the fruit of FIG. 8a.

FIG. 9a is a computer image of fruit having split or cut in the peel as determined according to the invention, while

FIG. 10a is a computer image of fruit with clear puff and crease as determined according the invention, while FIG. 10b is a histogram taken along a selected scan line of the fruit of Figure 10a.

Figure 1:
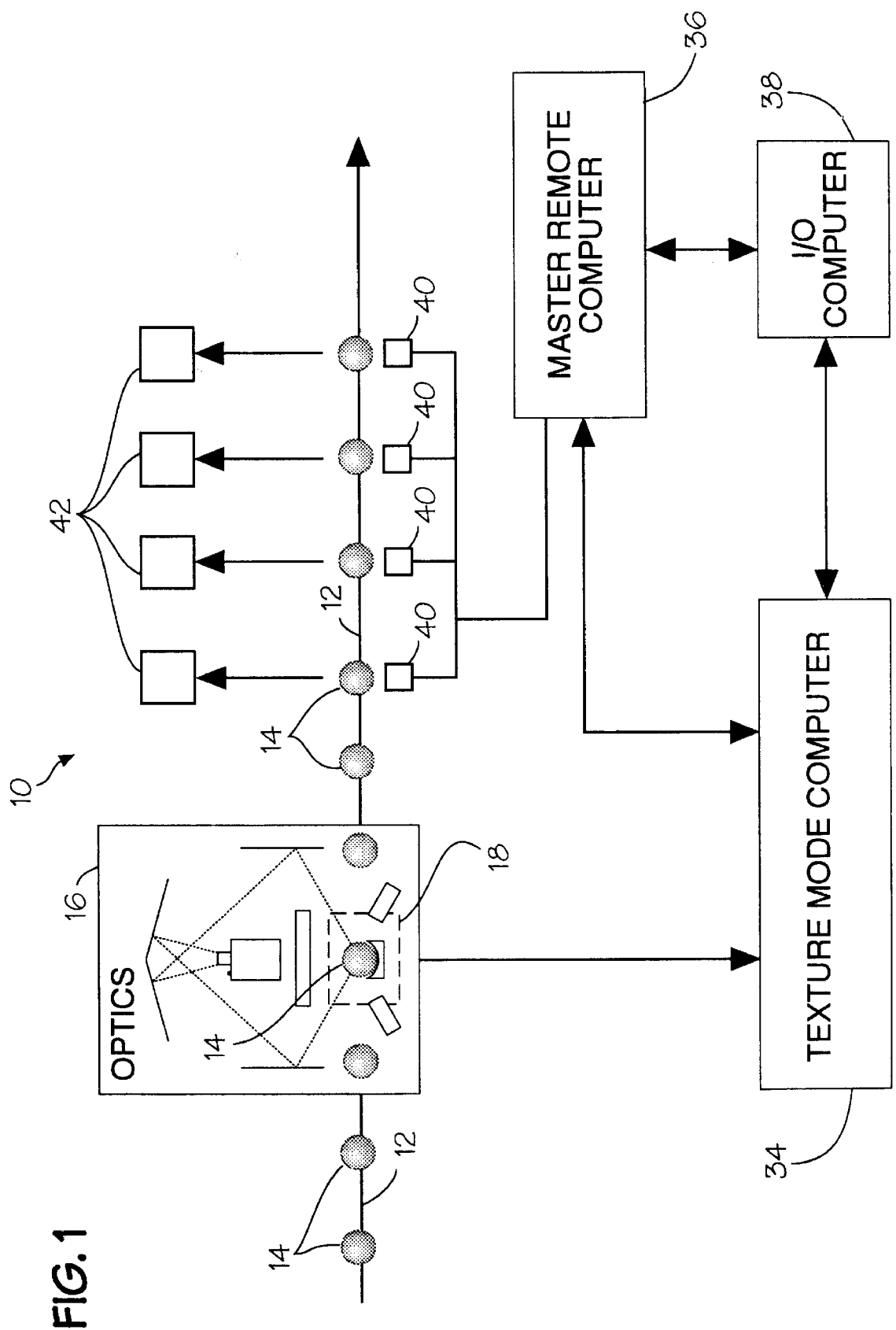
FIG. 1 is a simplified block diagram of a classification and sorting apparatus using a texture mode computer according to the invention.

The invention and its various embodiments may now be understood by turning to the following detailed description.

DETAILED DESCRIPTION OF THE PREFERRED EMBODIMENTS

It is believed important, at this juncture, to clarify certain terminology which may have been used hereinabove and which may be used hereinbelow.

Accordingly, "transmitted light" is light which passes through a medium essentially as a beam, which may or may not have "spread" as the result of its passage through the medium. Also contemplated within this term is that remaining portion of the incident light which, after some of the intensity present in the incident beam has been scattered or absorbed, continues to pass "forward" through the medium.

For the purposes of this discussion, "scattered" light is light which has spread away from the direction of the incident beam. It is primarily this scattered light which causes the glow in translucent objects.

By "absorbed" light is meant light from the incident beam which is neither transmitted through nor scattered within the medium, but whose energy is instead retained by the medium.

Reference is herein made to "translucent" objects. By these references is meant objects within which light of a selected frequency or spectrum from an incident beam may be partially absorbed and partially scattered, but from which at least some of the scattered light can be detected externally because of passage through the surface region thereof. Typical examples are fruit (such as pumpkins, melons or citrus fruit), wax, certain ceramics, certain plastics and composites (fibrous materials combined with a castable resin), where the selected frequencies might normally be the visible spectrum, the near infrared or perhaps other frequencies.

By a "transparent" object is meant an object which allows substantially free transmission of incident light of a selected frequency or frequencies therethrough primarily in a beam (which may spread), which transmitted light is not primarily absorbed or scattered within the object. A typical example would be ordinary window glass, where the frequencies are the visible sprectrum and certain other frequencies.

A transparent object at least a portion of whose surface region is translucent or absorbs light is, for the purposes of interpreting the Specification, Claims and Abstract hereof, considered to be a translucent object, since some light scattering or absorption would occur in such an object, at least in the surface region thereof, and this would permit application of the methods and apparatus of this invention. An example of such an object would be a plastic ball, where the interior—air—would be transparent to visible light, whereas the surface region—plastic—would be translucent to visible light. Another example would be a sheet of glass, bearing imperfections, such as scratches, warps or spots, on its surface. Such imperfections would scatter and/or absorb some of the light transmitted through the glass. This would enable it to be classified and sorted according to the teachings of this invention.

In general, therefore, it will be understood by those with reasonable skill in the art to which this invention pertains, that many types of objects can be classified and sorted in accordance with these teachings. For our purposes, all such objects are to be considered as included within the term "translucent", and are definitive thereof.

Reference to objects herein can therefore be understood to include any object falling within the foregoing definitions, including, but not limited to, citrus fruit. Likewise, reference to fruit or citrus fruit herein can be understood to refer to any object which might be classified and sorted according to the method and apparatus of this invention.

By the "surface region" of an object is meant a region of the object at its outer periphery which may have appreciable thickness, such as the peel of a citrus fruit, and also includes the outer surface of such an object. Thus, "surface" and "surface region" are essentially synonymous. Indeed, whether a fruit defect exists merely on the outer surface, or "within" the surface may make little practical difference in the market value of the fruit, if evidence of it can be visually detected at the outer surface.

The terms "puff", "crease", "clear rot", "sour rot", "pebbled surface" and those other topographic and features and features relating to peel integrity used herein are well known in the citrus industry, and are given merely as examples of features which can be detected and upon which fruit (or other objects) may be classified according to this invention.

The topographic surface features of an object, in particular a spherical object such as a citrus fruit with a peel, are scanned and evaluated to permit the sorting of the objects according to their surface features. In the case of citrus fruit, the coarseness or pebbliness, puff and crease, ridge and valley, cuts, punctures, scrapes and splits, clear rot or sour rot of the peel is optically identified through digital analysis of the pixel scans and sorted based upon the peel surface region quality.

The objects are classified by segmenting the scanned image thereof into the background image and the image of the object itself. The background image is then removed. A statistical evaluation of the image of the object as a whole, including both hemispheres of the object, is then made to determine if there is any surface feature variation which might qualify as a defect or be a suitable basis upon which a classification judgment can be made. If there is, then the object image is subject to high frequency or low pass filtering and thresholding of the pixel intensities to derive a refined image. The refined image is then tabulated or organized into neighborhoods contiguous to sharp transitions or gradual transitions, to identify specific areas defined as blobs, which when compared against a selected minimum area, shape requirement and/or width can be identified as one of the surface imperfections described above.

FIG. 1 is a block diagram of a classification and sorting apparatus incorporating the texture computer and methodology of the invention. The classification and sorting apparatus, herein sometimes referred to as the "system" and generally denoted by reference numeral 10, includes a conventional conveyor line 12 upon which a plurality of objects 14 is conveyed. As pointed out above, objects 14 in the illustrated embodiment may be fruit, or more particularly citrus fruit, or any other type of essentially translucent or transparent object. Any such object, in particular any such spherical object having a topographic surface texture, could be equivalently processed by system 10.

Conveyor 12 transports fruit 14 into an optical housing 16, where the fruit is illuminated at an inspection station 18 within housing 16. Conveyor 12 transports and orients the fruit to control the presentation of the fruit for imaging. The conveyor is designed to provide a maximum optical exposure of fruit 14 at inspection station 18. Conveyor system 12 in the illustrated embodiment includes driven spools to rotate fruit 14. In the illustrated embodiment, fruit 14 is rotated in a retrograde direction as it moves through image station 18 in order to at least partially compensate for its forward motion down conveyor 12. In other words, the fruit is rotated so that the same surface tends to remain facing camera 30 during an extended time exposure to allow complete and reliable imaging. This may, of course, be time-synchronized by means well known in the art.

Figure 2A:
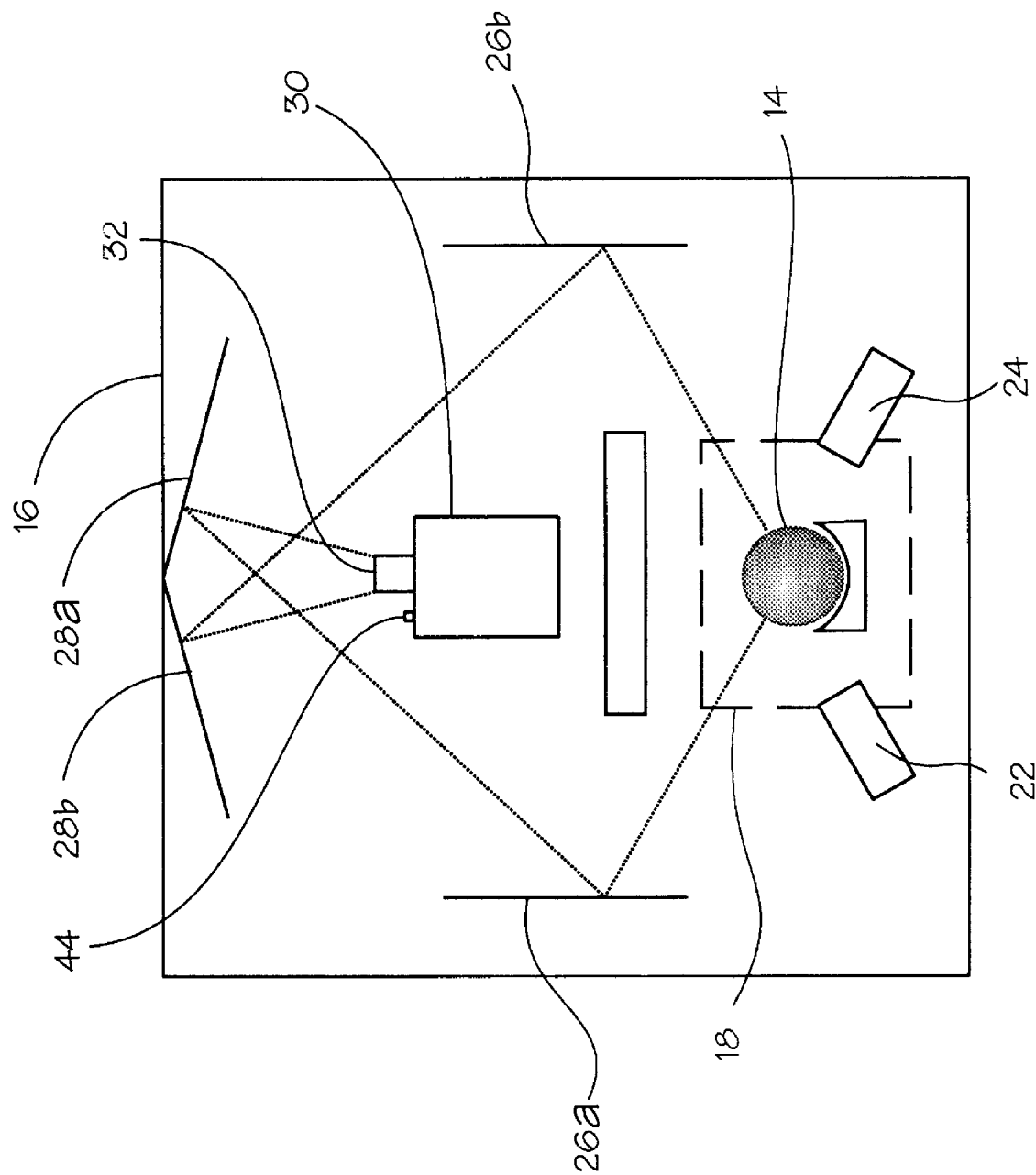
FIG. 2a is a simplified diagrammatic cross-sectional view of the optical housing used in the system of FIG. 1.

Optic housing 16 is perhaps better depicted in the simplified cross-sectional view of FIG. 2a, which shows fruit 14 carried by conveyor 12 into housing 16 to station 18, whereupon fruit 14 is illuminated by a pair of high intensity light sources 22 and 24. Light sources 22 and 24 are focussed on fruit 14 from below and may further be provided with conventional optics to assist in providing optimal illumination of the surface of fruit 14.

Alternatively, high intensity optical sources 22 and 24 may be replaced by two or more optical fibers which either may side illuminate fruit 14 or be placed at a lower inclined angle to project upwardly to illuminate as little of the fruit's outer surface as possible.

As further alternatives, optical sources 22 and 24 may be laser beams or light beams formed by LED's. Furthermore, a single light source may be utilized and may be optically divided into two optical sources 22 and 24 or more. In any event it is to be understood these optical sources 22 and 24 or a single light source provide the incident light which will be scattered within the fruit to cause it to glow. And, as previously suggested, the frequency or frequency spectrum of the light is selected, based on the optical properties of the object to be inspected, to produce the desired scattering within the object, and the resultant projection of that glow through the surface thereof. With citrus fruit, the ordinary visible spectrum could suffice.

For certain applications, it may be desired to use a specific wavelength or spectrum of incident light, so that a desired optical effect may accentuate the particular type of defect in that type of object to be monitored. It is left to the reasonably skilled practitioner, faced with the particular type of object and defect, to determine the correct frequency or spectrum of the incident light.

Inspection station 18 is appropriately baffled as desired, either to provide flat black nonreflecting surface to avoid spurious images, or to include reflective surfaces if desired to increase the light intensity incident upon the fruit. In any case, in the embodiment illustrated in FIG. 2a, the glow from light scattered within fruit 14 and projected through its peel is reflected from lower mirrors 26a and b, and thence to upper mirrors 28a and b. As further shown in FIG. 2a, A CCD matrix or scanning camera 30 has its optics 32 focused upon upper mirrors 28a and b to capture, in a single computer image, virtually the entire exterior surface of a hemisphere of fruit 14, as depicted in FIGS. 3a–10a.

Figure 2B:
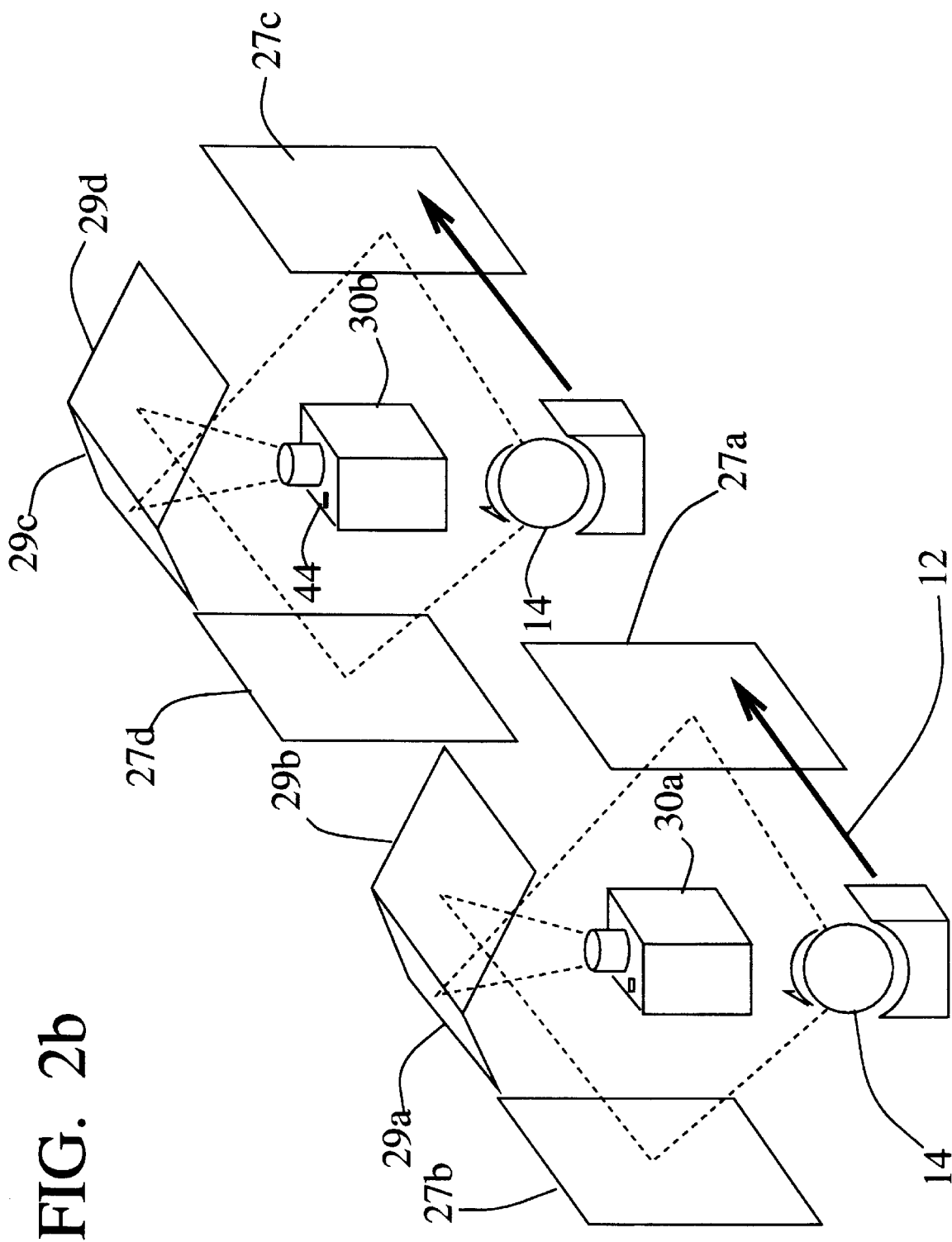
FIG. 2b is a simplified isometric plan view of a second embodiment of the optical housing used in the system of FIG. 1.

As shown in FIG. 2b, there are actually two cameras 30a and b, each of which captures an image of one of the two hemispheres. For example, the first hemispheric image of fruit 14 as seen in FIG. 2b is reflected by lower right mirror 27a to upper left mirror 29a and thence to the first camera 30a. The image of that first hemisphere is also reflected by lower left mirror 27b into upper right mirror 29b in the first camera 30a.

Then, after the fruit 14 has proceeded down the conveyor and experienced a synchronized rotation to expose its other hemisphere, the image of that second hemisphere of fruit 14 is reflected by lower right mirror 27c to upper left mirror 29c, and from lower left mirror 27d to upper right mirror 29d, both resultant images being reflected into the other camera 30b.

As shown in FIG. 1, Camera 30 is coupled to a texture mode computer 34. Texture mode computer 34 is a personal computer coupled both to a master remote computer 36 which runs the necessary functions of the conveyor and sorting systems and to an input/output computer 38, which provides user input and output access to system 10. The texture analysis of fruit 14 is made within texture mode computer 34. According to user instructions, input through input/output computer 38 to master remote computer 36 will implement a sorting operation as dictated by texture mode computer 34 at a plurality of sorting stations 40, which may include solenoid actuated ejection fingers upon which fruit 14 rides, and by which fruit 14 is ejected from conveyor line 12 into appropriate sorting bins 42 or secondary conveyors. Such ejection is described by LaVars et al in "Conveyor Discharge Apparatus and Method".

U.S. Pat. No. 5,174,429 (1992). Thus, it can be understood by viewing FIG. 1 that the texture module of system 10 is made up of three subsystems which includes the lighting and optics including optical housing 16, imaging as provided by cameras 30 and mirrors 26a and b, and 28a and b, and image processing within texture mode computer 34.

Central input/output computer 38 and master remote computer 36 are conventional and are substantially the same as used in prior art classification and sorting apparatus. For this reason, these portions of system 10 will not be further described in any detail other than to provide a background to support the description of the operation of texture mode computer 34. Central input/output computer 38 provides for system control including providing for all aspects of user interface, selection for input and output of various classification parameters, and for determining conveyor paths in system 10 where multiple lanes for conveyor 12 are provided in a more complex array than the simple linear depiction illustrated in FIG. 1.

The lighting system uses two tungsten Halogen projection lamps 22 and 24 situated on opposite sides of fruit 14 and below the fruit centerline. The use of any particular type of lamp or illuminating system is not mandated by the design requirements of system 10, nor is the number of lamps. The only requirement is that the lamp or lamps emit enough light of the proper frequency or spectrum incident on the fruit to create a glowing effect transmitted through the peel of fruit 14 that can be detected by a camera. In other words, the fruit will provide a glowing effect to the camera provided that the positioning, intensity and frequency/spectrum of the light is such that the light penetration into the peel or rind of fruit 14 occurs and is scattered therewithin to provide a glowing effect through the peel.

There is no special filter on the camera, and time exposure of the imaging is electronically controlled. Electronic control of the time exposure compensates for any difference in the intensity of the glow due to differences in fruit size and peel thickness. This can be determined during the initial part of the run and appropriate corrections, either automatic or manual, may be entered through input/output controller 38.

Automatic control may be effected by use of a photodiode 44 mounted on each camera 30 to generate an output frequency, by a frequency generator (not shown), which depends upon the amount of light sensed by each photodiode. By using the output frequency from the frequency generator controlled by photodiodes 44, the exposure time on the CCD chip within cameras 30 is controlled.

There are a large number of ways in which fruit 14 may be illuminated, as well as ways in which a computer image may be taken of fruit 14, either with the use of one or more cameras and various optical systems and configurations. It is not intended to limit the scope of the invention by being restricted to the illustrated optical system, illumination system or imaging system. Instead, it is expressly contemplated that many other variations and approaches may be equivalently employed to obtain the results required by the invention. All that is required, in the preferred embodiment, is that a substantially complete computer image of each fruit 14 be provided so that texture characterizations as discussed below will not omit any significant portion of the fruit surface. Indeed, for some applications, an image of one hemisphere only, using a single camera 30 and simplified optics, may be sufficient.

Texture mode computer 34 performs image processing and passes the classification information to the rest of the system for final drop-out selection according to means known in the art. The actual method or algorithm by which image processing is practiced is not critical and can be widely varied depending upon the power and capability of the processor used within texture mode computer 34 and its controlling software. In the illustrated embodiment, texture mode computer 34 utilizes a model TMS320C40 microprocessor, manufactured by Texas Instruments, to provide imaging processing through an algorithm generated using a general image processing development package sold under the trademark KB Vision by Amerinex Artificial Intelligence, Inc. of Maryland.

Figure 3A:
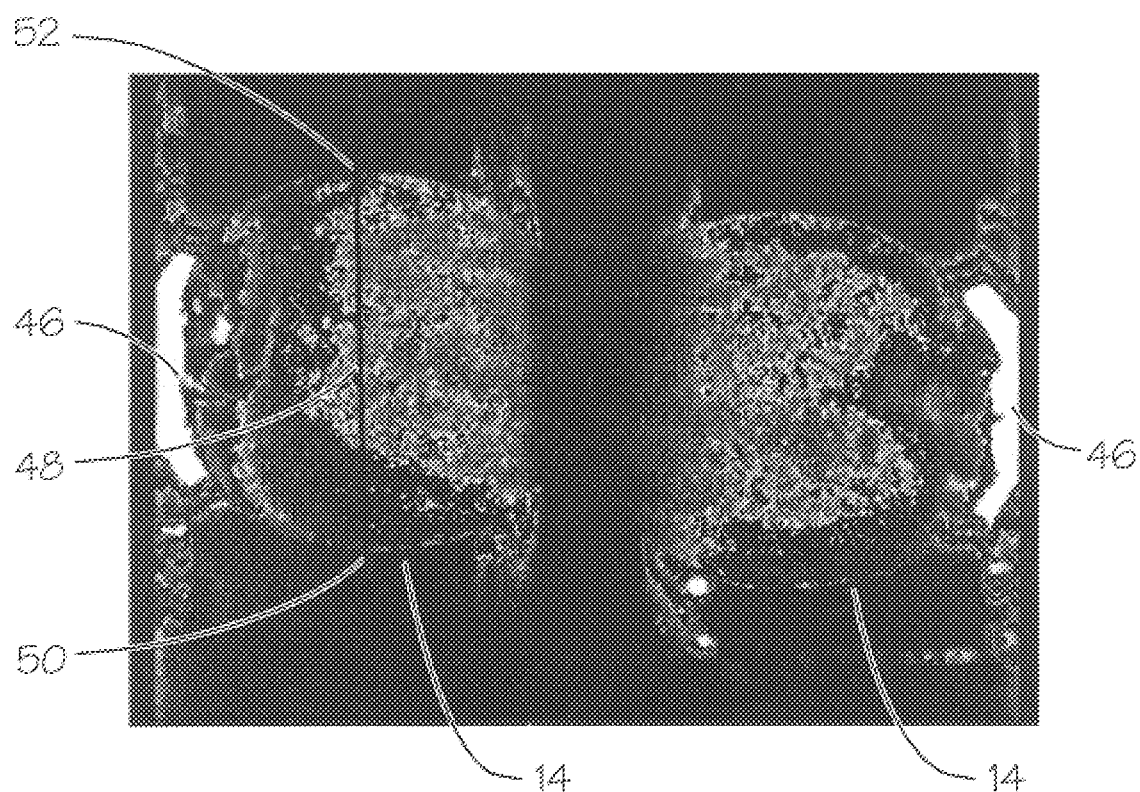

The basic hardware of system 10 having been described, we now consider in general how the captured image is processed to provide topographic surface texture grading. In the illustrated embodiment, the first step in processing is to drop out invalid information such as reflected light intensities from light sources 22 and 24 which do not constitute the glow from light scattered within the fruit 14 and emerging through its peel. Turning for example to FIG. 3a, bright portions 46 of an actual computer image of a smooth fruit peel are depicted. Two images of fruit 14 are shown in FIG. 3a, depicting in essence the two hemispherical views of the fruit. Thus, regions 46 of the graphic image, because of their distinctively higher intensity levels, can be eliminated as portions of the graphic information signal carrying no information about the topographic surface texture.

Next, an entire scan of the fruit surface is made to provide maximum, minimum and standard deviation of the intensity of the entire pixel pattern constituting the image, to provide an indication if there are intensity variations in the image which could constitute surface defects requiring further examination, such as puff and crease, cuts, punctures or rot.

A puff in a citrus fruit is an area of the peel which is slightly detached from the underlying meat, and thus will be slightly swollen or puffed out. A crease is the reverse, in which a portion of the rind surface has been depressed compared to adjoining areas.

If no defects are detected, then the graphic image is checked for high frequency data which, for example, would be indicative of pebbliness of the fruit surface. The data derived from the fruit 14 can then be fed back to the master remote computer 36 for classification purposes according to user criteria.

In an instance where global statistical analysis of the fruit surface indicates that peel defects exist, the type of defect can then be determined by applying a series of data filters to identify them. The high pass data filter can be used to search for cuts or punctures. A low pass filter with blob analysis, tracing and aspect ratio of areas of greater intensity is useful to identify puff and crease and to distinguish it from rot. A blob is defined herein as a contiguous area of the peel that has a topographic surface texture of one category.

After the puff and crease data is separated, a series of checks to show peak intensities over standard deviation values can be used to identify the degree of defect within a category of defect, such as puff and crease. After all this processing is done, the size of the fruit as a whole is then compared with the area affected in order to generate a percentage value for the defect of the affected surface. Other defects, such as rot or breaks in the rind may not be subject to a percentage evaluation, but constitute a cause for immediate rejection of the fruit regardless of the percentage of the affected area of the fruit.

How this processing may be effected can be better appreciated by now viewing FIGS. 3a–10a in comparison to their pixel intensity histograms taken on selected scan lines as shown in the corresponding FIGS. 3b–10b, respectively. We turn first to FIG. 3a, in which a computer image of a smooth orange rind is depicted, illustrating the double image from the reflected image provided to the camera. As previously discussed, brightened areas 46 from the illumination source are eliminated as not containing information relevant to the nature of the peel condition.

Statistical information is then taken of the entire graphic image to obtain maxima, minima, and standard deviations to characterize the intensity variations of the image pixels. In this case, the statistical deviations which would be returned would indicate that the fruit was smooth and well within the acceptable range. At that point, further statistical analysis would be unnecessary, and the fruit position tagged within system 10 and carried down conveyor 12 to be routed to the appropriate sorting bin 42 or secondary conveyor, or for analysis and classification according to additional methods and criteria.

For the purposes of illustration, a typical scan line 48 is taken across one portion of the two hemispherical images in FIG. 3a. Scan line intensity is then depicted in the histogram of FIG. 3b where intensity is graphed against the vertical scale and positioned along the scan line along the horizontal scale with end 50 corresponding to the left end of the histogram of FIG. 3b and end 52 of scan line 48 corresponding to the right end of the histogram of FIG. 3b. A visual examination of the histogram of FIG. 3b indicates variations of pixel intensity maintained within a range of values with a fairly limited deviation from a mean, to provide a pattern quite different from the histograms depicted in FIGS. 4b–10b, wherein various fruit defects are illustrated. Through conventional statistical measures, the histograms of FIGS. 3b–10b can be characterized by meaningful statistical parameters, and through those parameters, sorted into categories to reliably identify the topographic surface texture of fruit 14.

Further, although a single scan line is depicted on one of the hemispherical images of fruit 14 in FIG. 3a, it is expressly understood that multiple scan lines 48 at different directions and positions taken across each of the hemispheric images could be taken in order to obtain an average statistical definition of the topographic surface texture of fruit 14.

Figure 4A:
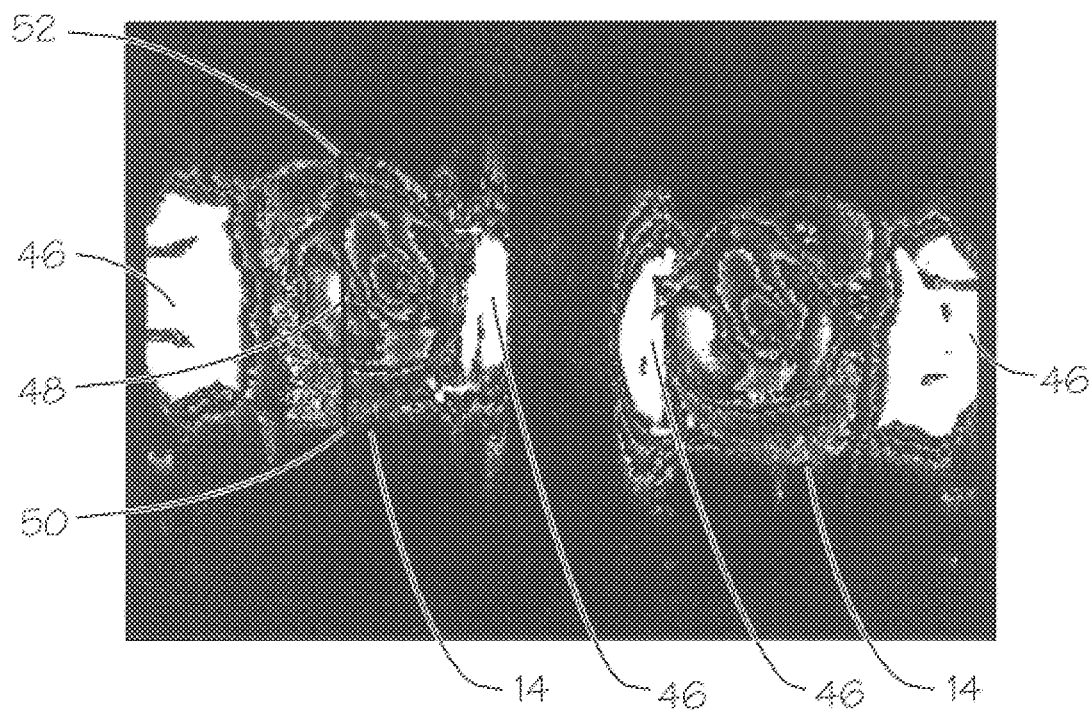

FIG. 4a illustrates a computer image of a fruit 14 blemished by a surface decomposition known as sour rot, which is visible in the topographic surface texture. Again, bright illumination areas 46 are eliminated from the image as being irrelevant. Overall statistical analysis is made, indicating that there is sufficient pixel variation in the topographic surface texture to require further data processing for skin blemishes. A typical scan line 48 is consequently taken across one of the hemispherical images of fruit 14, and its corresponding intensity histogram plotted in FIG. 4b to show the intensity varying from the bottom of the scan line in FIG. 4a (i.e., the left of the histogram of FIG. 4b) to the top 52 of scan line 48 in FIG. 4a (i.e., the right of the histogram in FIG. 4b).

Figure 3B:
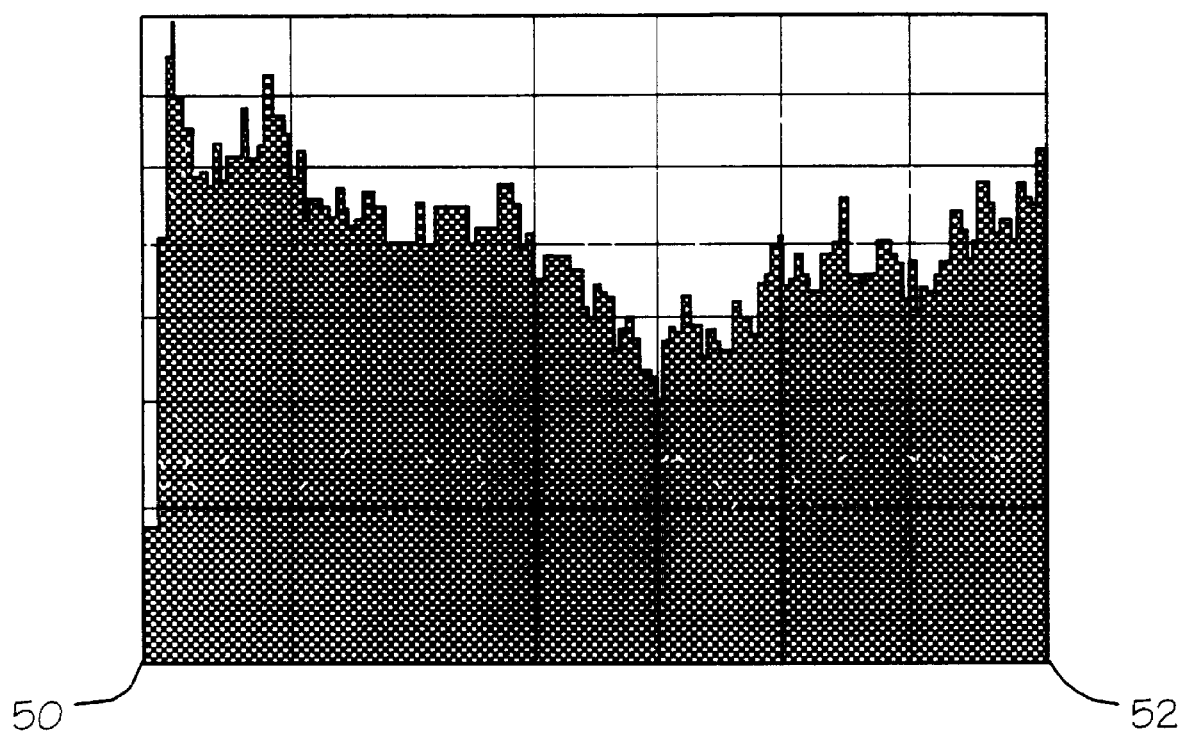
FIG. 3b is the corresponding histogram of the fruit surface as taken along a selected scan line.
Figure 4B:
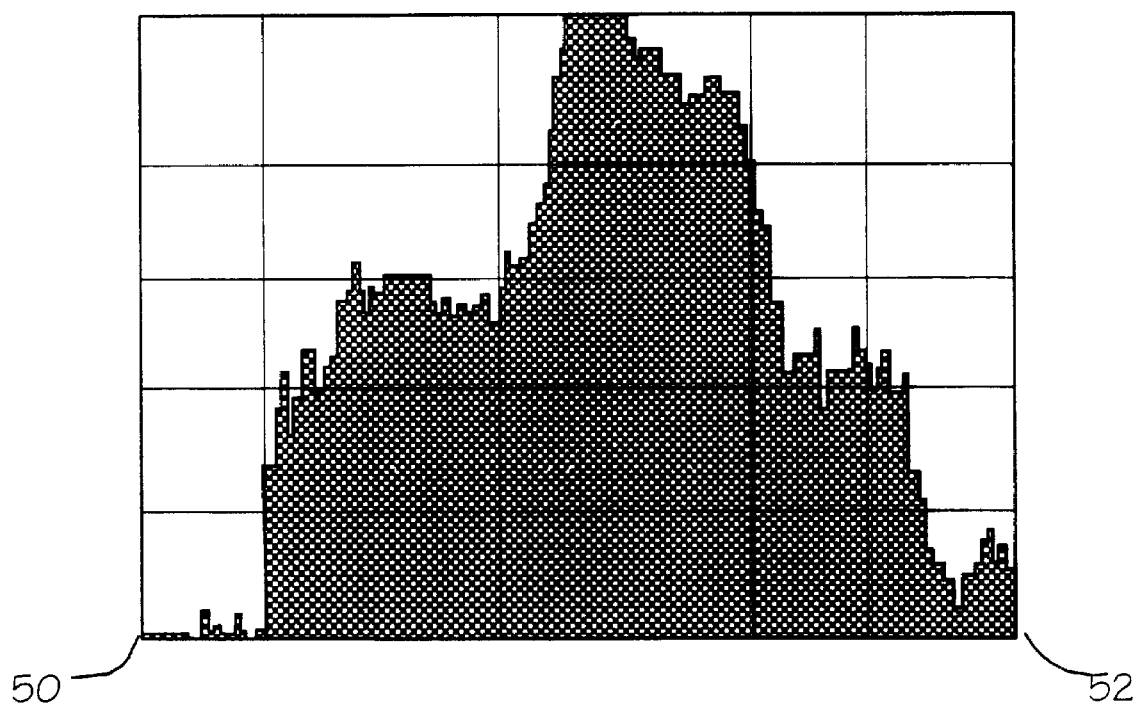

Comparison of the pixel intensity histograms of FIGS. 3b and 4b immediately show a clear and definite difference in the pattern character. There is a much wider variation between maxima and minima, and deviation from the mean is much greater than in FIG. 3b. The image is processed to identify areas of gradual transitions in pixel intensity. A predetermined threshold is established, either automatically (based on statistical measures) or set by the user through central input/output computer 38. The number of pixels having an intensity above the predetermined threshold in neighborhoods contiguous to pixel boundaries with gradual transitions is tabulated. These neighborhoods are defined as blobs. The number of blobs which exceed a given characteristic parameter used to identify the surface defect are then tabulated. If this number exceeds a given maximum percentage of the peel area, the fruit is tagged and tracked for rejection.

Recognition of pattern shapes of the histograms can also be performed within texture mode computer 34 through conventional curve fitting techniques. The sour rot histogram is characterized by a large central peak falling off steeply to plateau shoulders. Multiple scan lines 48 can be taken through both hemispherical images of fruit 14 if desired. The fruit in detection position 18, having a pixel intensity histogram of this shape, can then be marked as blemished by sour rot and carried by conveyor 12 and sorted appropriately into a collecting bin 42 or secondary conveyor under the control of master remote computer 36 acting on parameters set in response to central input/output computer 38 which is given the texture mode characterization from texture mode computer 34.

Figure 5A:
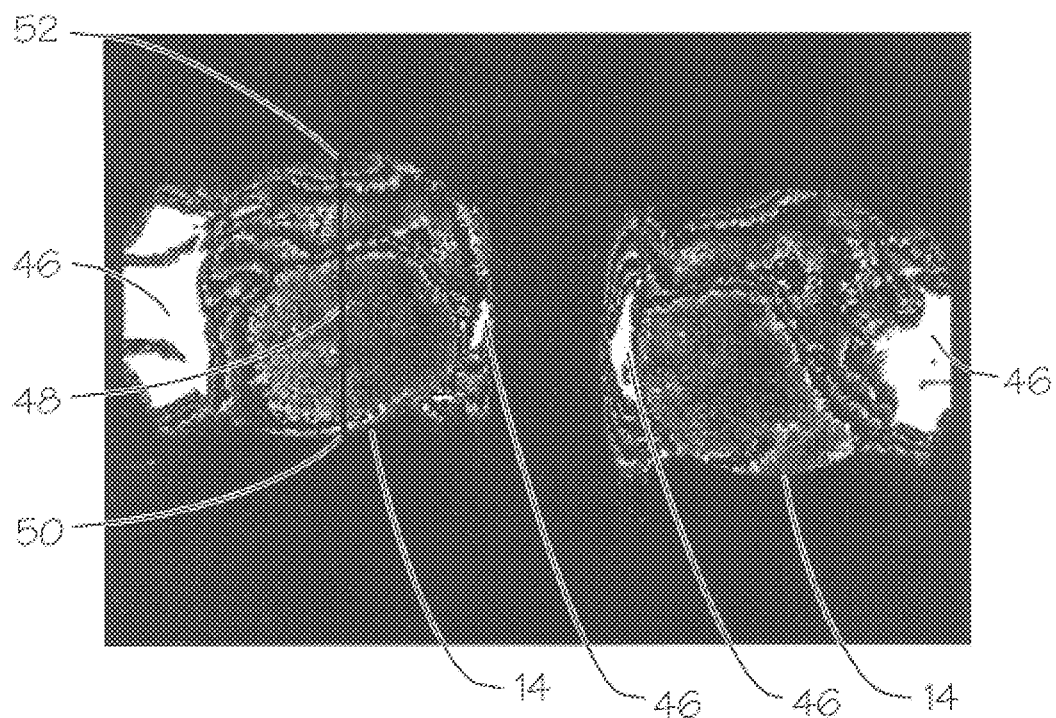
Figure 5B:
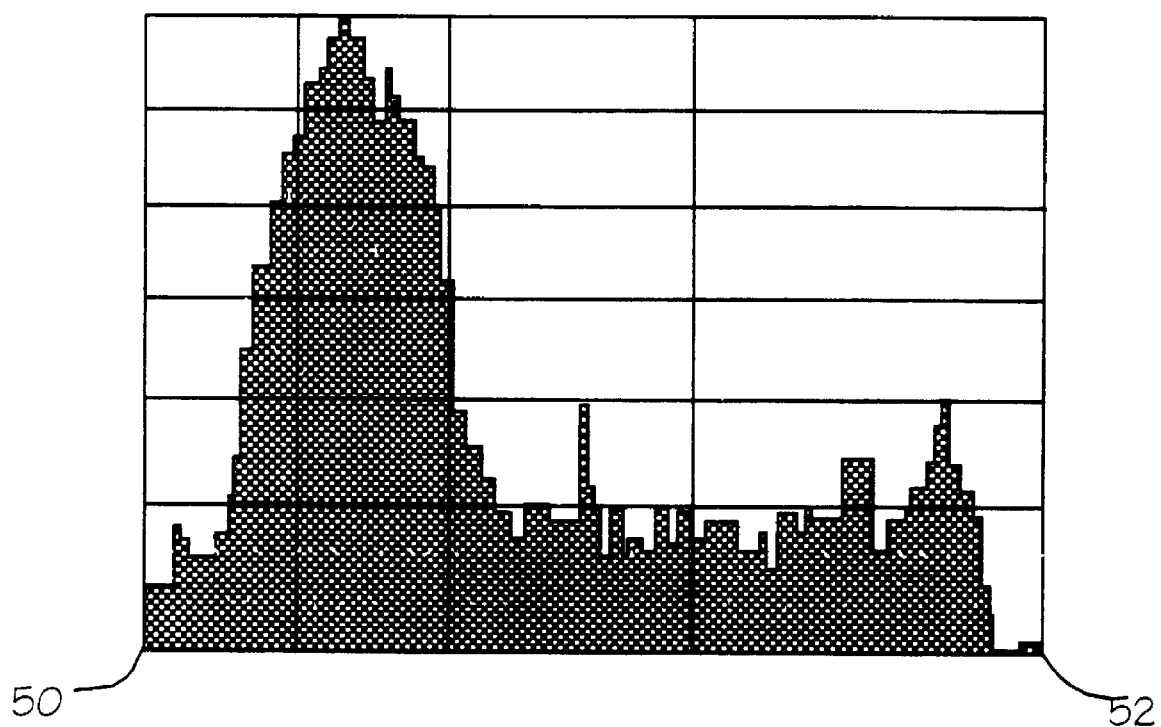

Similarly, FIG. 5a is a computer image of the two hemispheres of fruit 14 with a fruit characterized by a clear rot skin blemish. The corresponding histogram shown in FIG. 5b is characterized by a large peak sharply falling off to an average pixel intensity elsewhere in the scan line off the clear rot spot. Again, this image is distinct from that of FIGS. 3b and 4b and can be distinctly recognized through conventional pattern recognition, the fruit marked and sorted accordingly in system 10. The processing of the image for clear rot is similar to that described above for sour rot.

Figure 6A:
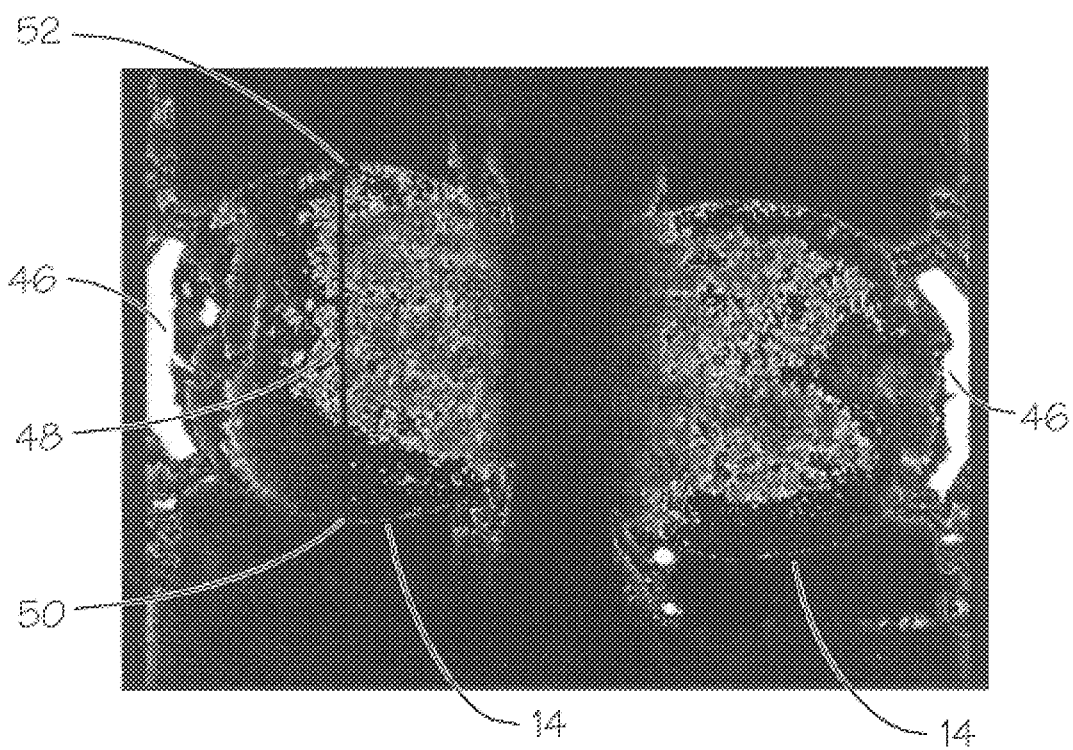
Figure 6B:
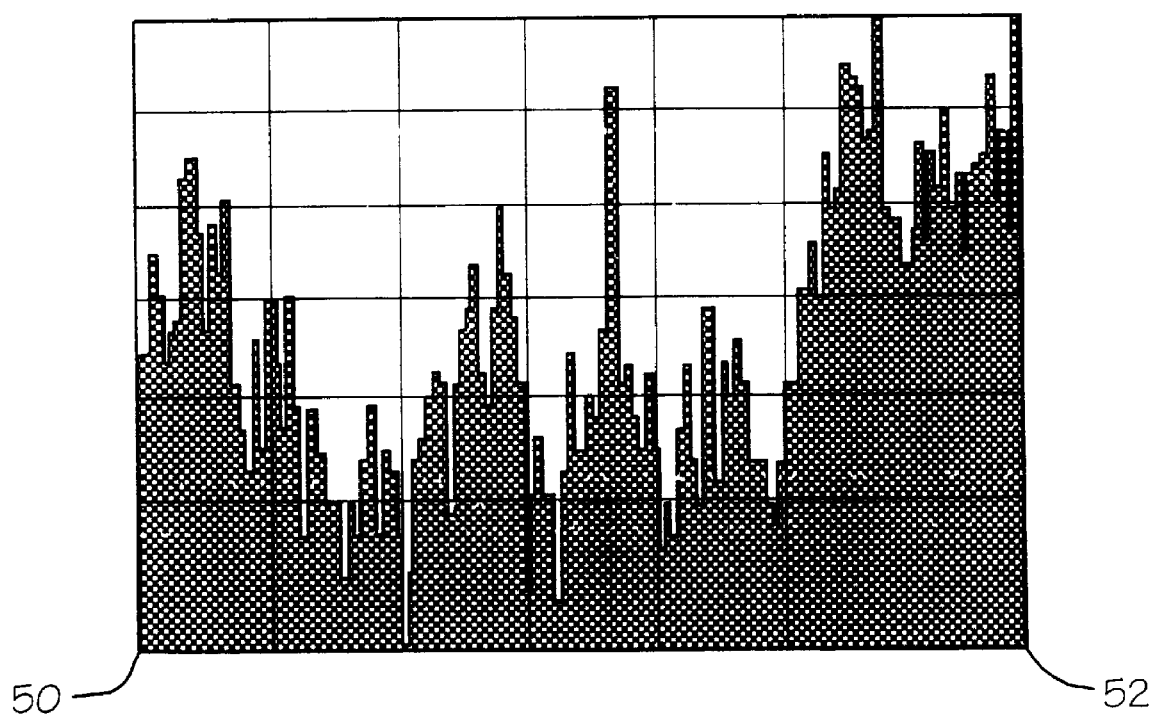
FIG. 6b is a histogram of the topographic surface texture of the fruit of FIG. 6a taken along a selected scan line.

FIG. 6a is a computer image of fruit 14 having a high porosity or a pebbled surface, which in some markets, consumers may consider less than perfect. The corresponding histogram is shown in FIG. 6b, which illustrates a scattered variation of high pixel intensities, resulting in a forest of skyscrapers of thin width separated by deep valleys. The histogram of FIG. 6b is distinct from the patterns of FIGS. 3b–5b and, through statistical and pattern recognition, can be identified and fruit 14 appropriately classified and sorted in system 10. In particular, the scanned image is filtered to leave high frequency data using a high pass data filter. A threshold of pixel intensity of said filtered image is established and the number of pixels having an intensity above such threshold is tabulated to assess the porosity of the peel.

Figure 7A:
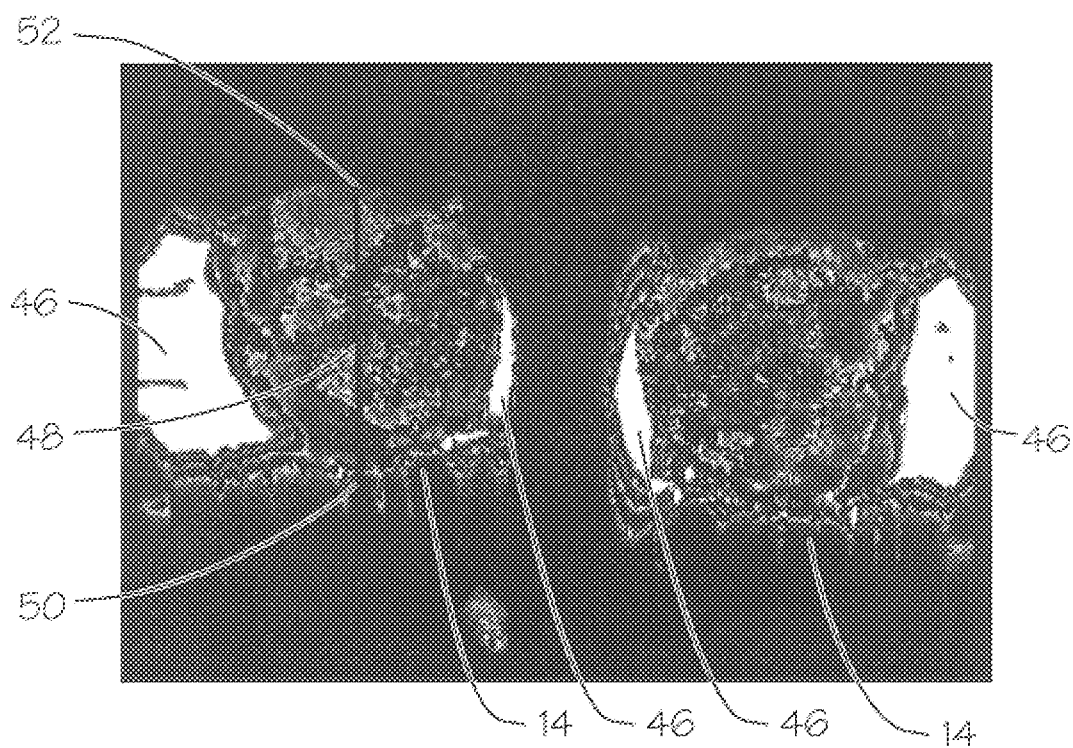
Figure 7B:
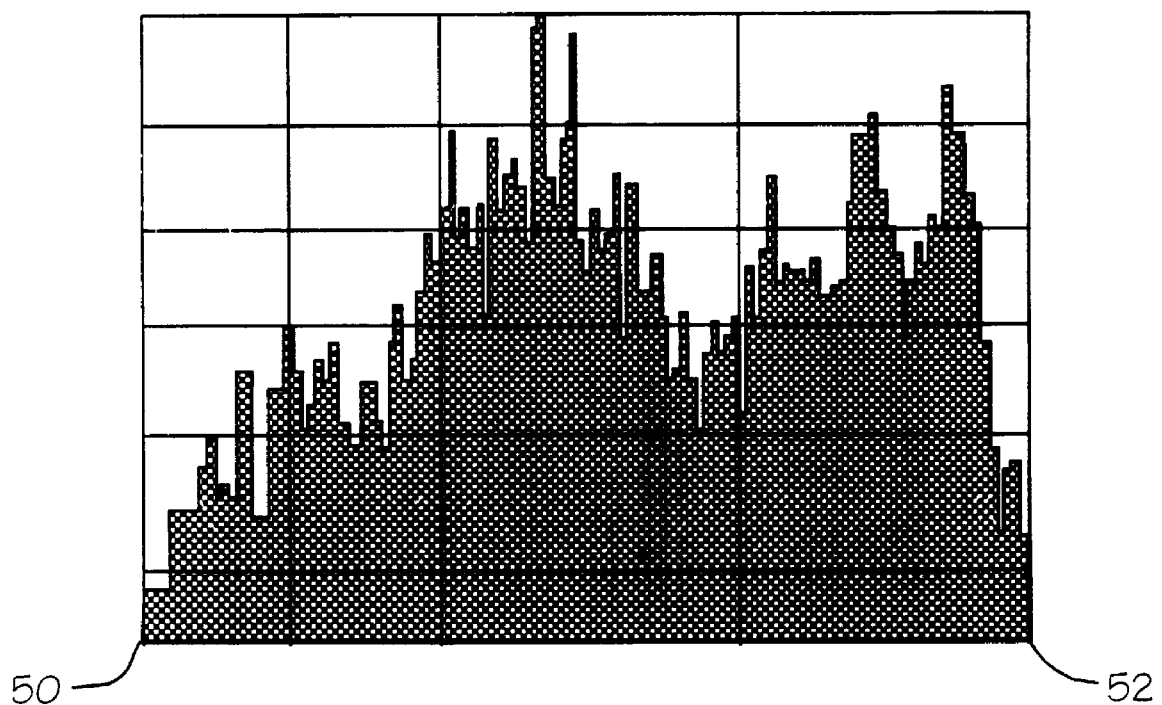
FIG. 7b is a histogram of the topographic surface texture of the fruit of FIG. 7a taken along a selected scan line.

FIG. 7a shows a computer image of fruit 14 whose surface is characterized by the surface blemish known as soft puff and crease, or is characterized by hills and valleys in the peel topography. The corresponding histogram is shown in FIG. 7b, as seen along typical scan line 48 of FIG. 7a. The histogram shape is distinct from that of FIGS. 3b–6b, being characterized by a plurality of high peaks, some with medium widths separated by valleys of medium depths. Again, the histogram of FIG. 7b can be statistically and pattern recognized to allow tagging of fruit 14 with the soft puff and crease defect and to thereby allow its selective sorting into the appropriate collection bin 42 or secondary conveyor of system 10. In particular, the image is filtered for low frequency data using a low pass data filter or any data processing algorithm which smooths or softens the pixel data intensities. A pixel intensity threshold is established for the filtered image, and the number of pixels having an intensity above that threshold is tabulated to identify hills and valleys in the peel.

Figure 8A:
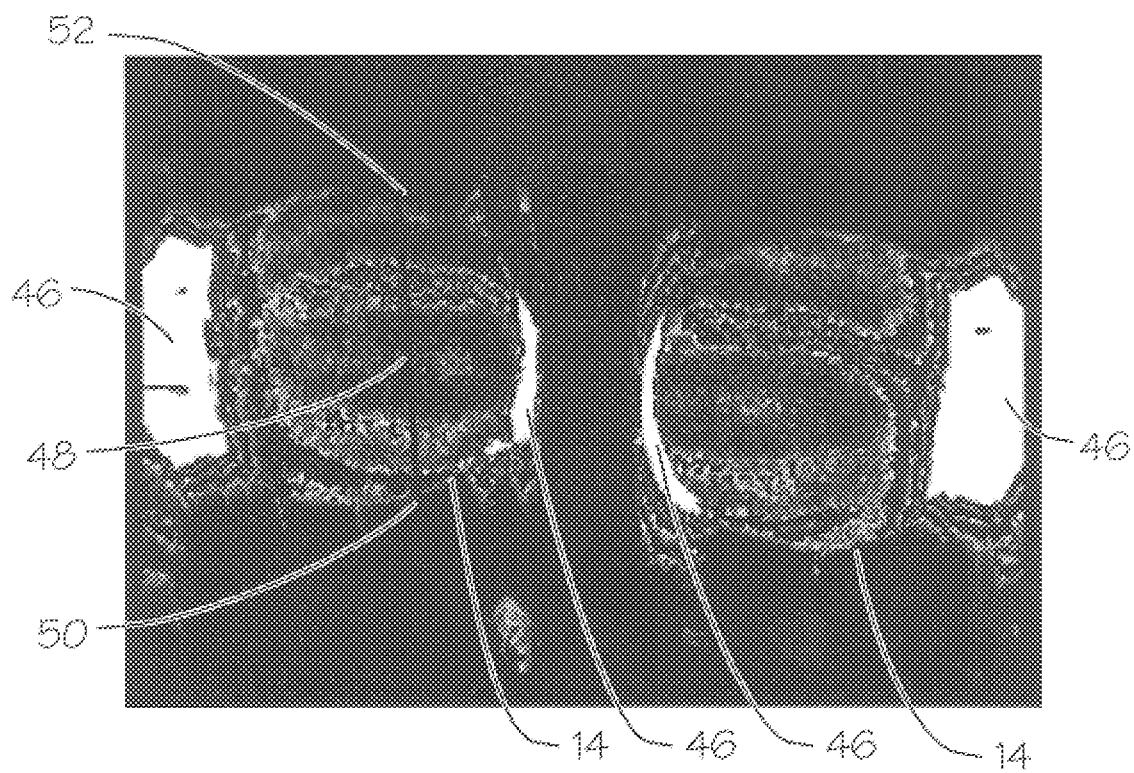
Figure 8B:
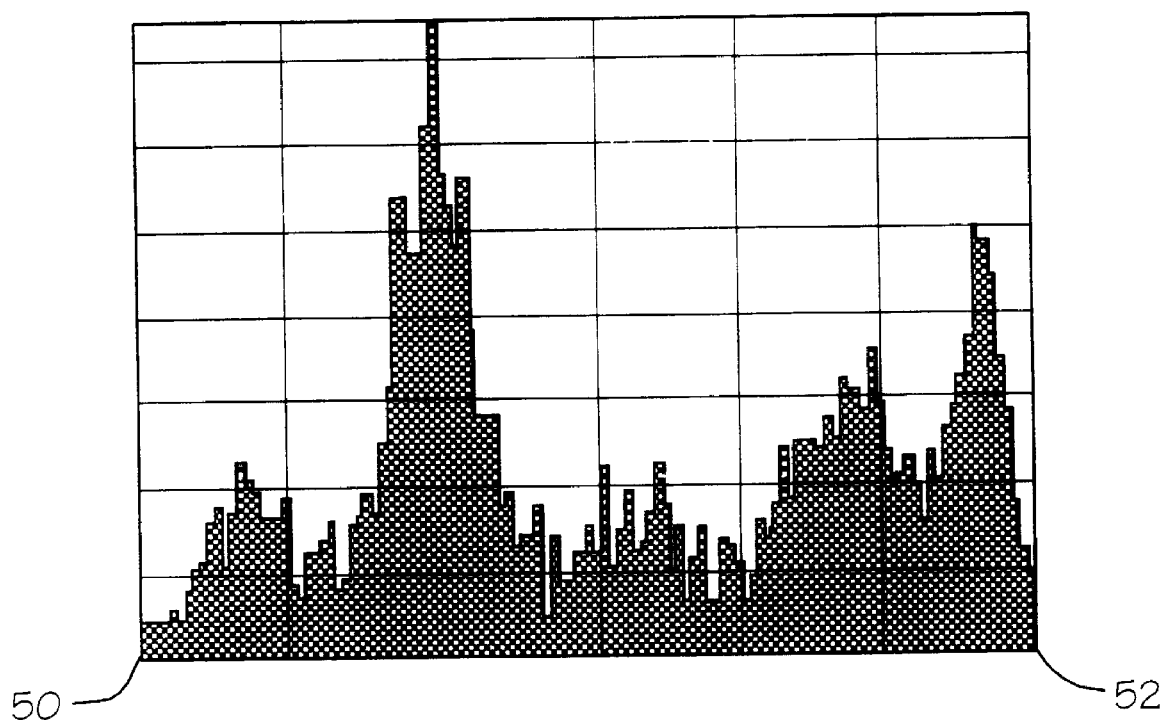

FIG. 8a shows the graphic image of the two hemispheres of a fruit 14 whose skin is blemished by a defect known as ridge and valley. These are longitudinal valleys or ridges formed on the outside of the peel during growth. The corresponding histogram is shown in FIG. 8b and is again a distinct pattern from the histograms of FIGS. 3b–7b, characterized by wide and high peaks with deep valleys between them, corresponding to the ridges and valleys formed in the fruit peel. The fruit is correspondingly graded according to statistical and pattern recognition and sorted by system 10. In particular, the image is selectively scanned for sharp transitions in pixel intensity. A threshold of pixel intensity is established. The number of pixels having an intensity above the established threshold in neighborhoods contiguous to pixel boundaries corresponding to sharp transitions is tabulated. The neighborhoods are defined as blobs. The number of blobs which exceed a predetermined characteristic parameter used to identify raised and recessed wedges in the peel are then tabulated. Again, as in all of the cases of FIGS. 3a–10a, an absolute number of blobs or percentage of the total peel area within blobs is determined to provide a criterion by which the fruit is accepted, rejected or otherwise handled.

Figure 9A:
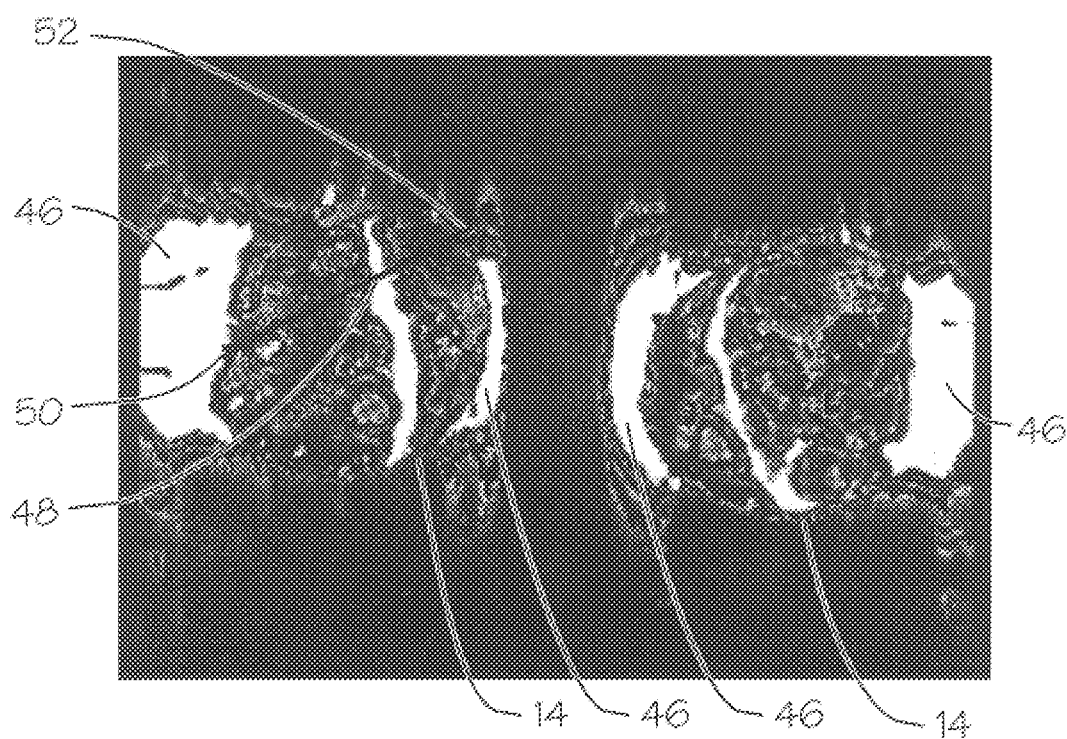
Figure 9B:
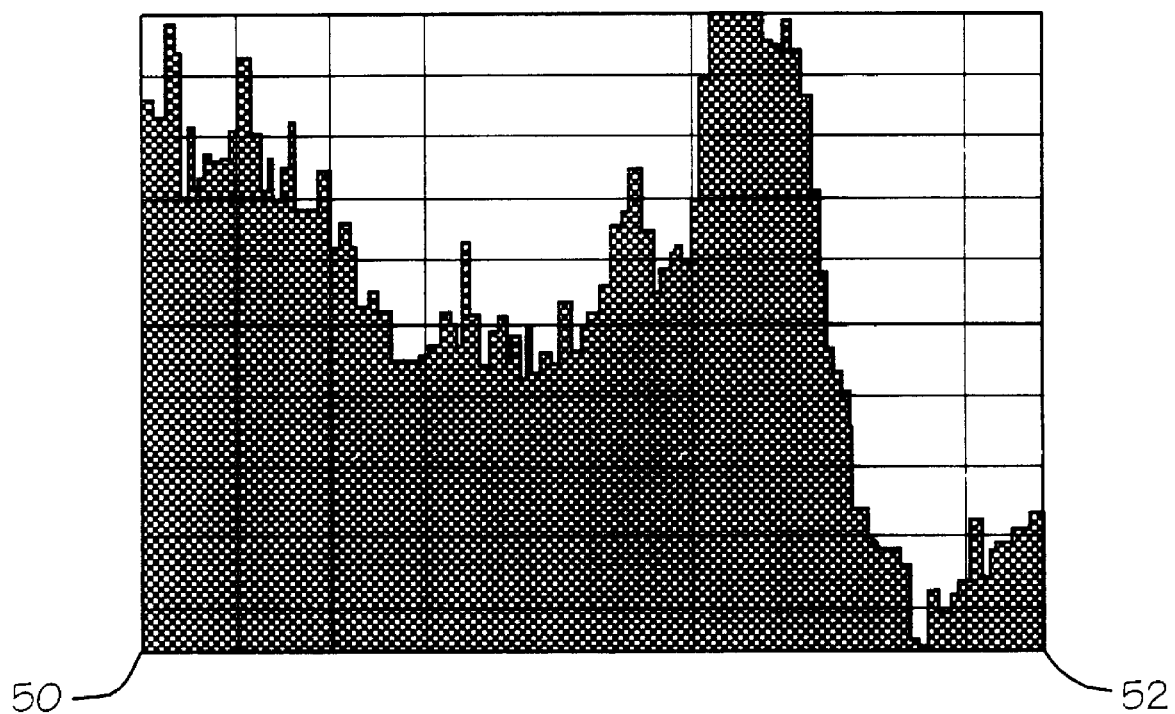
FIG. 9b is a histogram of the texture of the fruit of FIG. 9a taken along a selected scan line.

FIG. 9a shows fruit images 14 for a piece of fruit exhibiting "fractures", generically defined to include splits, cuts, punctures and scrapes. The corresponding histogram is shown in FIG. 9b and is characterized by very large and wide peaks with deep and wide adjacent valleys. The histogram is visually, statistically and pattern distinct from the histograms shown in FIGS. 3b–8a, and allows fruit 14 to be classified and sorted appropriately within system 10. In particular, the image is scanned for sharp transitions in pixel intensity. A predetermined threshold is provided. The number of pixels having an intensity above the predetermined threshold in neighborhoods continuous to pixel boundaries with sharp transitions is tabulated. The neighborhoods are defined as blobs. The number of the blobs which exceed a predetermined area and predetermined width are tabulated to identify fractures in said peel.

Figure 10A:
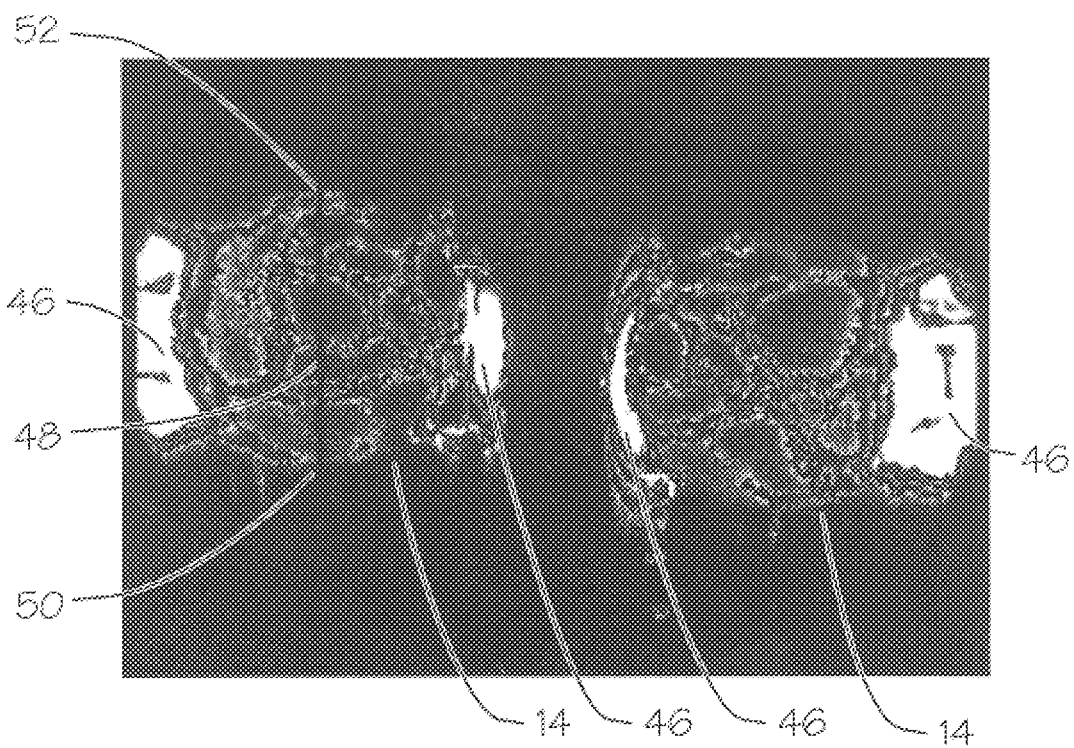
Figure 10B:
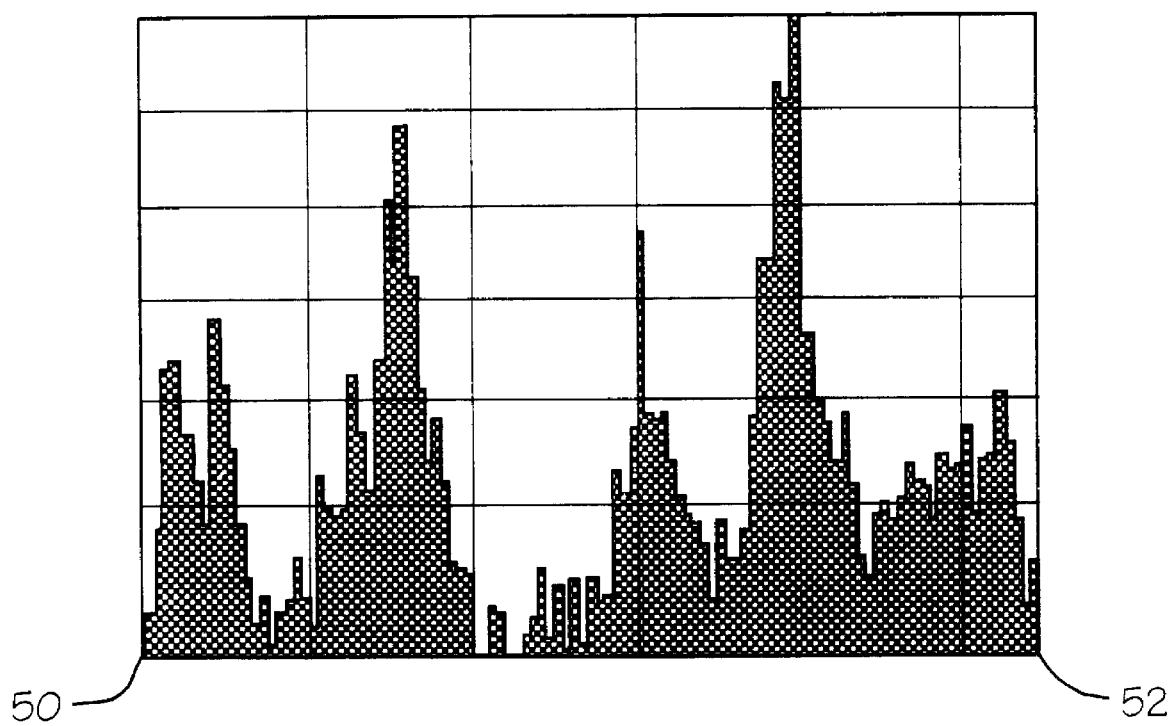

FIG. 10a is a computer image of the two hemispheres of a fruit 14, characterized by clear puff and crease skin defect. The corresponding histogram is shown in FIG. 10b, and provides a distinctive pattern of high multiple peaks of medium width with narrow apexes separated by deep valleys, which is a statistically and pattern distinct image from that shown in FIGS. 3b–9b. Accordingly, fruit 14 with clear puff and crease can be selectively classified and sorted in system 10. The image processing is substantially the same as practiced with soft puff and crease described above.

Figure 11:
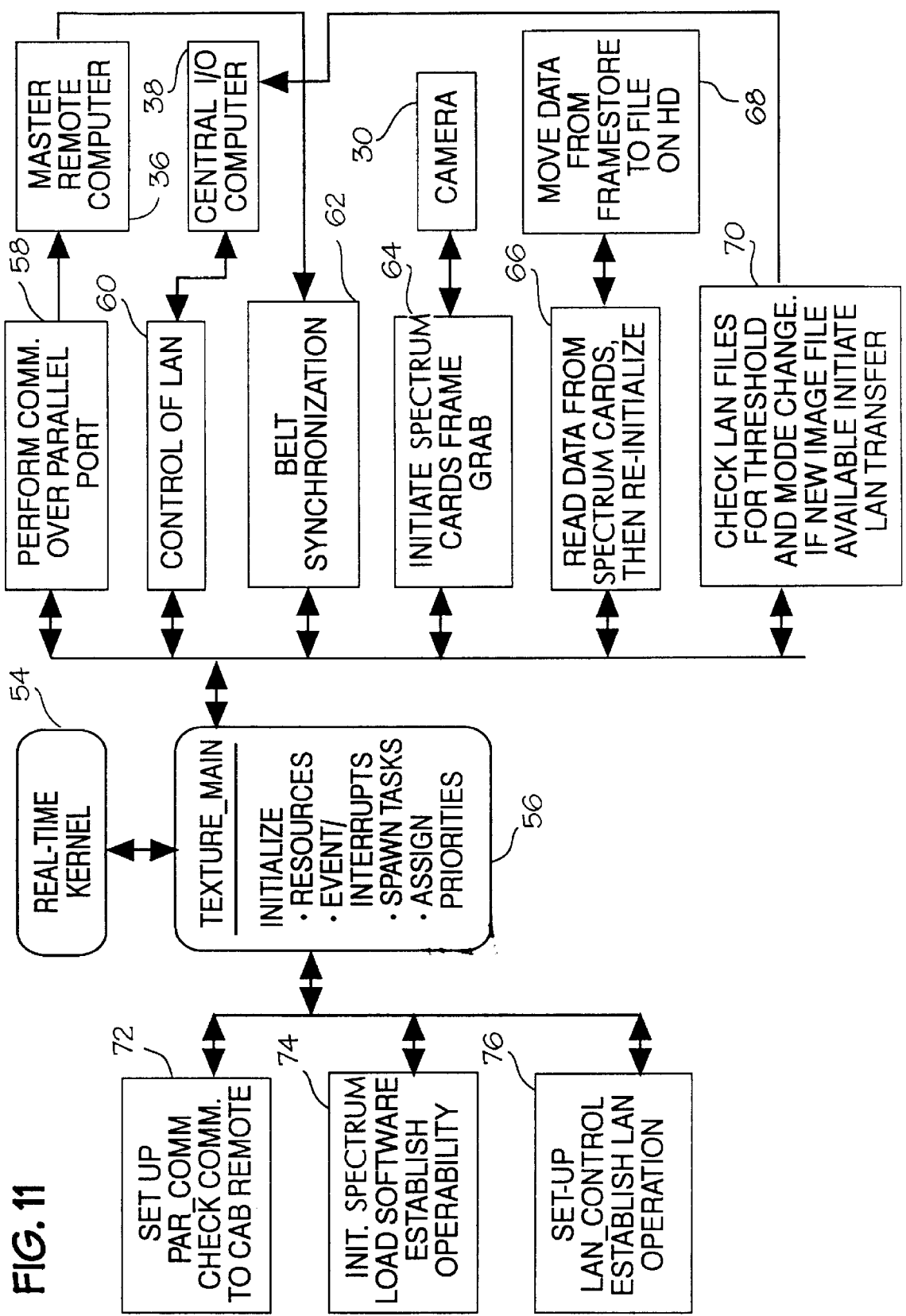
FIG. 11 illustrates a diagram of the software control of the present invention.

The hardware of system 10 and the processing of the image data now having been described, we consider the overall software architecture by which the data processing is achieved. The operation of system 10, and in particular, the software control of texture mode computer 34, is illustrated by the software architectural diagram of FIG. 11. The software organization of FIG. 11 shows the major modules used by texture mode computer 34 to perform the operations described above.

A real time kernel 54 provides the operating system of the illustrated embodiment. A main texture module 56 performs initialization tasks, manages the various resources coupled to the texture mode computer 34, handles event interrupts which requires special processing, spawns or assigns system tasks which must be performed and assigns priorities among competing software requests within the texture mode computer 34.

Main texture module 56 communicates in parallel with the plurality of other modules or resources. For example, module 56 communicates through a parallel communication port module 58 for control and data communication with master remote computer 36. Communication with central input/output computer 38 is handled through a local area network module 60. Movement and synchronization of the conveyor 12 is tracked through a belt synchronization module 62, which is also in communication with master remote computer 36 to receive information concerning conveyor speed and position.

Camera 30 communicates with texture mode computer 34 in an efficient graphic frame grab protocol under the control of module 64, which is used to initiate and monitor operation of the video frame grab card, which, in the illustrated embodiment, is a SPECTRUM video card manufactured by Spectrum Signal Processing, Inc. of British Columbia, Canada.

Processed graphic data is read from the video card by module 66 and stored for archival data purposes on a hard disk under the control of data handling module 68. The processed image data, such as seen in FIGS. 3a–10a, is transferred to central input/output computer 38 for user information by means of a local area network transfer module 70. This allows the operator to see the same processed images being seen by texture module 56 in system 10 while the system is in operation.

Additional housekeeping software tasks are handled by a setup of module 72 which sets up and monitors communication with computers 36 and 38 and other systems with which system 10 may be combined. For example, the grading and sorting of system 10 may be combined with a system for grading color and blemishes of the citrus fruit as described in U.S. Pat. No. 5,164,795, communication with which color and blemish grader is set up by means of utility module 72. Module 74 provides initialization of the video card and confirmation of its operability. Utility module 76 similarly sets up and establishes local area network control and operation.

It is to be clearly understood that the software system and its organization can be widely varied while still performing the same essential functions of collecting graphic data, processing the data to characterize the category or nature of topographic surface texture, and providing the characterization to a central computer 38 and a master remote computer 36 for appropriate decision and routing according to user selection.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition structure, material or acts beyond the scope of the commonly defined meanings. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements thereof.

The claims are thus to be understood to include what is specifically illustrated and described above, what is conceptually equivalent, what can be obviously substituted and also what essentially incorporates the essential idea of the invention.

We claim:

1. A method of classifying a translucent object having a surface with at least one of a plurality of possible surface feature patterns, said object being classified according to said at least one possible surface feature pattern, comprising the steps of:

illuminating the object to cause light to be scattered therewithin;

detecting such scattered light transmitted through the surface of the object;

converting such detected light to data representing the relative intensity of light transmitted through each of a plurality of defined areas of the surface;

analyzing such data to determine the existence of said at least one surface feature pattern; and classifying the object on the basis of determination of said surface feature pattern, wherein said step of analyzing the data comprises deriving a statistical measure of the data characteristic of said at least one surface feature pattern in order to identify said at least one surface feature pattern from among said plurality of surface feature patterns possible for said object, wherein the step of detecting further comprising the step of optically forming an image of the transmitted scattered light from the object, and wherein said object is illuminated with a source having an optical beam and said step of optically forming an image comprises optically reflecting an image of only the scattered light transmitted from the object into a camera pointed away from the object and not in said optical beam of said source.

2. A method of classifying a translucent object according to at least one selected surface feature of the object, comprising the steps of:

illuminating the object to cause light to be scattered therewithin;

detecting such scattered light transmitted through the surface of the object;

converting such detected light to data representing the relative intensity of light transmitted through each of a plurality of defined areas of the surface;

analyzing such data to determine the existence of the selected feature of the surface; and classifying the object on the basis of such determination, wherein a plurality of surface features are considered, and said step of analyzing comprises determining if any of such surface features exists on the object, wherein the object is a citrus fruit with a peel, and wherein said step of analyzing comprises determining the extent of porosity of the peel of the citrus fruit.

3. A method of classifying a translucent object according to at least one selected surface feature of the object, comprising the steps of:

illuminating the object to cause light to be scattered therewithin;

detecting such scattered light transmitted through the surface of the object;

converting such detected light to data representing the relative intensity of light transmitted through each of a plurality of defined areas of the surface;

analyzing such data to determine the existence of the selected feature of the surface; and classifying the object on the basis of such determination, wherein a plurality of surface features are considered, and said step of analyzing comprises determining if any of such surface features exists on the object, wherein the object is a citrus fruit with a peel, and wherein said step of analyzing comprises determining the extent of puff and crease in the peel of the citrus fruit.

4. A method of classifying a translucent object according to at least one selected surface feature of the object, comprising the steps of:

illuminating the object to cause light to be scattered therewithin;

detecting such scattered light transmitted through the surface of the object;

converting such detected light to data representing the relative intensity of light transmitted through each of a plurality of defined areas of the surface;

analyzing such data to determine the existence of the selected feature of the surface; and classifying the object on the basis of such determination, wherein a plurality of surface features are considered, and said step of analyzing comprises determining if any of such surface features exists on the object, wherein the object is a citrus fruit with a peel, and wherein said step of analyzing comprises determining the extent of ridges and valleys in the peel of the citrus fruit.

5. A method of classifying a translucent object according to at least one selected surface feature of the object, comprising the steps of:

illuminating the object to cause light to be scattered therewithin;

detecting such scattered light transmitted through the surface of the object;

converting such detected light to data representing the relative intensity of light transmitted through each of a plurality of defined areas of the surface;

analyzing such data to determine the existence of the selected feature of the surface; and classifying the object on the basis of such determination, wherein a plurality of surface features are considered, and said step of analyzing comprises determining if any of such surface features exists on the object, wherein the object is a citrus fruit with a peel, and wherein said step of analyzing comprises determining the extent of fractures in the peel of the citrus fruit.

6. A method of classifying a translucent object according to at least one selected surface feature of the object, comprising the steps of:

illuminating the object to cause light to be scattered therewithin;

detecting such scattered light transmitted through the surface of the object;

converting such detected light to data representing the relative intensity of light transmitted through each of a plurality of defined areas of the surface;

analyzing such data to determine the existence of the selected feature of the surface; and classifying the object on the basis of such determination, wherein a plurality of surface features are considered, and said step of analyzing comprises determining if any of such surface features exists on the object, wherein the object is a citrus fruit with a peel, and wherein said step of analyzing comprises determining the extent of surface decomposition in the peel of the citrus fruit.

7. A method of classifying a translucent object according to at least one selected surface feature of the object, comprising the steps of:

illuminating the object to cause light to be scattered therewithin;

detecting such scattered light transmitted through the surface of the object;

converting such detected light to data representing the relative intensity of light transmitted through each of a plurality of defined areas of the surface;

analyzing such data to determine the existence of the selected feature of the surface; and classifying the object on the basis of such determination, wherein the step of detecting further comprising the step of optically forming an image of the transmitted scattered light from the object, and wherein said step of analyzing comprises: separating the image into a background image and an object image; and removing the background image, leaving an object image, wherein the object is a fruit with a peel and wherein said step of analyzing comprises determining the extent of porosity of said peel, and further comprising: scanning the object image; filtering the scanned image for high frequency data using a high pass data filter; establishing a threshold of pixel intensity of the filtered image; and tabulating a number of pixels having an intensity above the threshold.

8. A method of classifying a translucent object according to at least one selected surface feature of the object, comprising the steps of:

illuminating the object to cause light to be scattered therewithin;

detecting such scattered light transmitted through the surface of the object;

converting such detected light to data representing the relative intensity of light transmitted through each of a plurality of defined areas of the surface;

analyzing such data to determine the existence of the selected feature of the surface; and classifying the object on the basis of such determination, wherein the step of detecting further comprising the step of optically forming an image of the transmitted scattered light from the object, and wherein said step of analyzing comprises: separating the image into a background image and an object image; and removing the background image, leaving an object image, wherein the object is a fruit with a peel and wherein said step of analyzing comprises determining the existence of hills and valleys in the peel, and further comprising: scanning the object image;
filtering the scanned image for low frequency data using a low pass/smoothing data filter;
establishing a threshold of pixel intensity of the filtered image; and
tabulating the number of pixels having an intensity above the threshold.

9. A method of classifying a translucent object according to at least one selected surface feature of the object, comprising the steps of:

illuminating the object to cause light to be scattered therewithin;

detecting such scattered light transmitted through the surface of the object;

converting such detected light to data representing the relative intensity of light transmitted through each of a plurality of defined areas of the surface;

analyzing such data to determine the existence of the selected feature of the surface; and classifying the object on the basis of such determination, wherein the step of detecting further comprising the step of optically forming an image of the transmitted scattered light from the object, and wherein said step of analyzing comprises: separating the image into a background image and an object image; and removing the background image, leaving an object image, wherein the object is a fruit with a peel and wherein said step of analyzing comprises determining the existence of raised and recessed wedges in the peel, and further comprising:
selectively scanning the object image for sharp transitions in pixel intensity;
establishing a threshold of pixel intensity;
tabulating the number of pixels having an intensity above the threshold in neighborhoods contiguous to pixel boundaries corresponding to sharp transitions, said neighborhoods being defined as blobs; and
tabulating the number of blobs which exceed a predetermined characteristic parameter, whereby raised and recessed wedges in the peel are identified.

10. The method of claim 9 wherein the characteristic parameter comprises a selected minimum blob area, and said step of tabulating the number of blobs comprises tabulating the number of blobs exceeding the selected minimum area.

11. The method of claim 9 wherein the characteristic parameter comprises a selected blob shape, and said step of tabulating the number of blobs comprises tabulating the number of blobs complying with the selected shape definition.

12. A method of classifying a translucent object according to at least one selected surface feature of the object, comprising the steps of:

illuminating the object to cause light to be scattered therewithin;

detecting such scattered light transmitted through the surface of the object;

converting such detected light to data representing the relative intensity of light transmitted through each of a plurality of defined areas of the surface;

analyzing such data to determine the existence of the selected feature of the surface; and classifying the object on the basis of such determination, wherein the step of detecting further comprising the step of optically forming an image of the transmitted scattered light from the object, and wherein said step of analyzing comprises: separating the image into a background image and an object image; and removing the background image, leaving an object image, wherein the object is a fruit with a peel and wherein said step of analyzing comprises determining the existence of fractures in the peel surface, and further comprising: scanning the object image for sharp transitions and pixel intensity; establishing a selected threshold of pixel intensity of the object image; and tabulating the number of pixels having an intensity above the selected threshold in neighborhoods continuous to pixel boundaries with sharp transitions, such neighborhoods being defined as blobs; and tabulating the number of such blobs which exceed a selected area and width, whereby fractures in the peel are identified.

13. A method of classifying a translucent object according to at least one selected surface feature of the object, comprising the steps of:

illuminating the object to cause light to be scattered therewithin;

detecting such scattered light transmitted through the surface of the object;

converting such detected light to data representing the relative intensity of light transmitted through each of a plurality of defined areas of the surface;

analyzing such data to determine the existence of the selected feature of the surface; and classifying the object on the basis of such determination, wherein the step of detecting further comprising the step of optically forming an image of the transmitted scattered light from the object, and wherein said step of analyzing comprises: separating the image into a background image and an object image; and removing the background image, leaving an object image, wherein the object is a fruit with a peel and wherein said step of analyzing comprises determining the existence of surface decomposition, and further comprising:

scanning the object image for gradual transitions in pixel intensity;

establishing a selected threshold of pixel intensity;

tabulating the number of pixels having an intensity above the selected threshold in neighborhoods contiguous to pixel boundaries with gradual transitions, such neighborhoods being defined as blobs; and tabulating the number of such which exceed a given characteristic parameter, whereby surface decomposition is identified.

14. The method of claim 13 wherein the characteristic parameter comprises a selected minimum area of such blob, and said step of tabulating comprises tabulating the number of blobs which exceed the selected minimum area.

15. The method of claim 13 wherein the characteristic parameter comprises a selected shape, and said step of tabulating comprises tabulating the number of blobs having a shape complying with the selected shape definition.

16. An apparatus for identifying at least one selected surface feature pattern on a translucent object, said object having a plurality of possible surface feature patterns, comprising:

means for illuminating the object to cause light to be scattered therewithin;

means or detecting such scattered light transmitted through the surface of the object;

means for converting such detected light to data representing the relative intensity of light transmitted through each of a plurality of defined areas of the surface; and means for analyzing said data to derive a statistical measure of said data to identify said one of said surface feature patterns on said surface of said object, wherein said means for analyzing said data to derive a statistical measure of said data comprises means for forming a stored two dimensional digital image of said object, means for scanning said stored two dimensional digital image along a at least one straight line to obtain a scan of image intensity, means for generating a histogram of image intensity of said stored two dimensional digital image along said at least one straight line, and means for comparing said histogram to predetermined criteria to identify said one of said surface feature patterns.

17. The apparatus of claim 16 wherein said means for scanning scans said stored two dimensional digital image along a plurality of straight lines and averages said corresponding plurality of scans to obtain a scan of average image intensity from which said histogram is generated.

18. An apparatus for identifying at least one selected surface feature pattern on a translucent object, said object having a plurality of possible surface feature patterns, comprising:

means for illuminating the object to cause light to be scattered therewithin;

means for detecting such scattered light transmitted through the surface of the object;

means for converting such detected light to data representing the relative intensity of light transmitted through each of a plurality of defined areas of the surface; and means for analyzing said data to derive a statistical measure of said data to identify said one of said surface feature patterns on said surface of said object, wherein said means for detecting scattered light comprises a scanning camera directed at said object, but not in a line of sight with said means for illuminating said object, said scanning camera being otherwise shielded from said means for illuminating said object so that said scanning camera receives only signals scattered through said object and not from direct or reflected rays from said means for illuminating said object.

19. The apparatus of claim 18 wherein said scanning camera is turned diametrically away from said means for illuminating said object and further comprising an assembly of mirrors for reflecting only signals scattered through said object to said scanning camera.

* * * * *